(12) United States Patent
Jalgaonkar et al.

(10) Patent No.: US 11,058,848 B2
(45) Date of Patent: Jul. 13, 2021

(54) CATHETER INCLUDING EXPANDABLE MEMBER

(71) Applicant: Covidien LP, Mansfield, MA (US)

(72) Inventors: Ujwal Jalgaonkar, Irvine, CA (US); James Q. Dinh, Irvine, CA (US); Eric Rowson, Mansfield, MA (US)

(73) Assignee: Covidien LP, Mansfield, MA (US)

( * ) Notice: Subject to any disclaimer, the term of this patent is extended or adjusted under 35 U.S.C. 154(b) by 63 days.

(21) Appl. No.: 16/401,679

(22) Filed: May 2, 2019

(65) Prior Publication Data

US 2020/0345978 A1 Nov. 5, 2020

(51) Int. Cl.
*A61M 25/00* (2006.01)
*A61F 2/958* (2013.01)
(Continued)

(52) U.S. Cl.
CPC ......... *A61M 25/0023* (2013.01); *A61F 2/958* (2013.01); *A61M 25/0105* (2013.01); *A61M 25/1018* (2013.01); *A61M 2025/0024* (2013.01)

(58) Field of Classification Search
CPC .......... A61M 25/0023; A61M 25/0105; A61M 25/1018; A61M 2025/0024; A61M 2025/1068; A61M 25/04; A61M 25/0155; A61M 25/0133; A61M 25/104; A61M 2025/109; A61M 2025/1052; A61M 2025/1086; A61M 25/1002; A61M 2025/1093; A61M 1/008; A61M 2025/1015; A61M 25/0075; A61M 2025/0076; A61M 25/005; A61M 2025/004; A61M 2025/0042;
(Continued)

(56) References Cited

U.S. PATENT DOCUMENTS

| | | | |
|---|---|---|---|
| 4,794,928 A | 1/1989 | Kletschka | |
| 5,498,240 A * | 3/1996 | Bagaoisan | A61M 25/10 604/523 |
| 5,667,767 A | 9/1997 | Greff et al. | |
| 5,695,480 A | 12/1997 | Evans et al. | |

(Continued)

FOREIGN PATENT DOCUMENTS

| | | |
|---|---|---|
| EP | 1034752 A1 | 9/2000 |
| FR | 3003472 A1 | 9/2014 |

OTHER PUBLICATIONS

International Search Report and Written Opinion of counterpart International Application No. PCT/US2020/030043, dated Aug. 18, 2020, 14 pp.

*Primary Examiner* — Bhisma Mehta
*Assistant Examiner* — Robert F Allen
(74) *Attorney, Agent, or Firm* — Shumaker & Sieffert, P.A.

(57) ABSTRACT

A catheter includes an elongated body and an expandable member configured to expand radially outward away from the elongated body from a collapsed configuration to an expanded configuration. The catheter further includes a retainer configured to overlap an end of the expandable member to hold the expandable member in the collapsed configuration. The expandable member may be configured to engage with a vessel wall when the expandable member is in the expanded configuration. The vessel may curve and the expandable member may be configured to deflect a portion of the elongated body distal to the expandable member when the expandable member is engaged with the vessel wall to better conform the shape of the elongated body to the curved portion of the vessel.

27 Claims, 10 Drawing Sheets

(51) Int. Cl.
*A61M 25/01* (2006.01)
*A61M 25/10* (2013.01)

(58) Field of Classification Search
CPC .......... A61M 2025/0681; A61M 25/10; A61M 2025/0002; A61M 2025/1095; A61F 2/958; A61F 2/013; A61F 2/0105; A61F 2/01; A61F 2/011; A61F 2230/0006; A61F 2230/0067; A61F 2230/0076; A61F 2230/008; A61F 2002/018; A61B 2017/00938; A61B 2017/12054; A61B 17/2031; A61B 17/1204; A61B 17/12109; A61B 17/12172; A61B 17/12177; A61B 17/12136; A61B 17/22; A61B 17/221; A61B 17/12022; A61B 17/22031; A61B 17/3421; A61B 2017/22069; A61B 2017/00243; A61B 2217/005; A61B 2017/00292; A61B 2017/00778; A61B 2017/320716; A61B 2017/2215; A61B 17/00008; A61B 2017/22067; A61B 17/12; A61B 17/12045; A61B 8/06
See application file for complete search history.

(56) References Cited

U.S. PATENT DOCUMENTS

| | | |
|---|---|---|
| 5,755,658 A | 5/1998 | Wallace et al. |
| 5,785,642 A | 7/1998 | Wallace et al. |
| 5,830,178 A | 11/1998 | Jones et al. |
| 5,958,444 A | 9/1999 | Wallace et al. |
| 6,632,236 B2 | 10/2003 | Hogendijk |
| 6,695,858 B1 | 2/2004 | Dubrul et al. |
| 6,960,222 B2 | 11/2005 | Vo et al. |
| 2002/0143362 A1 | 10/2002 | Macoviak et al. |
| 2004/0210236 A1 | 10/2004 | Allers et al. |
| 2009/0240198 A1 | 9/2009 | Averbuch |
| 2011/0137399 A1* | 6/2011 | Chomas ............ A61M 25/0075 623/1.12 |
| 2012/0116351 A1* | 5/2012 | Chomas ................ A61F 2/2436 604/508 |
| 2012/0330346 A1 | 12/2012 | Frimerman |
| 2014/0277075 A1 | 9/2014 | Bonnette |
| 2015/0343178 A1 | 12/2015 | Fulton, III |
| 2017/0215900 A1 | 8/2017 | Lowinger et al. |
| 2017/0312069 A1 | 11/2017 | Sachar et al. |
| 2018/0296235 A1 | 10/2018 | Ulm, III |
| 2018/0296315 A1 | 10/2018 | Nguyen et al. |
| 2019/0269491 A1* | 9/2019 | Jalgaonkar ........ A61M 25/0074 |

* cited by examiner

CATHETER INCLUDING EXPANDABLE MEMBER

TECHNICAL FIELD

This disclosure relates to a medical catheter.

BACKGROUND

Medical catheters may be used in various medical procedures. For example, a medical catheter may be used to transport a fluid such as a drug or a medical agent (e.g., an embolic substance) to a target site within a patient. Additionally, or alternatively, a medical catheter may be used to transport an insertable or implantable medical device, a guidewire, or the like to a target site within a patient.

SUMMARY

In some aspects, this disclosure describes catheters that include an elongated body, an expandable member, and a retainer configured to hold the expandable member in a collapsed configuration. The expandable member is configured to expand radially outward away from the elongated body from a collapsed configuration to an expanded configuration while a first end of the expandable member is mechanically connected to the elongated body. The retainer may be configured to overlap a second end of the expandable member to hold the expandable member in the collapsed configuration. The expandable member may be configured to contact the inner walls of a vessel of a patient when the expandable member is in the expanded configuration. In some examples, the expandable member may be configured to deflect a portion of the elongated body distal to the expandable member when the expandable member contacts the inner walls of the vessel. In this way, the expandable member may aid navigation of the catheter through vasculature of a patient.

In some examples, the catheter further may include an occlusive material attached to the expandable member and configured to unfold or expand with the expandable member from a folded or collapsed configuration to an unfolded or expanded configuration that approximates the expanded configuration of the expandable member. When in the respective unfolded and/or expanded configurations, the occlusive material and the expandable member may be configured to provide a flow barrier to reduce or prevent antegrade blood flow within the vessel and/or to reduce or prevent retrograde flow of a fluid from the target vessel to a feeding vessel.

Clause 1: In one example, a catheter includes an elongated body; an expandable member extending from a first end to a second end, the first end of the expandable member being mechanically connected to the elongated body, wherein the expandable member is configured to expand radially outward away from the elongated body from a collapsed configuration to an expanded configuration; and a retainer configured to overlap the second end of the expandable member to hold the expandable member in the collapsed configuration.

Clause 2: In some examples of the catheter of clause 1, the first end of the expandable member is a proximal end and the second end of the expandable member is a distal end.

Clause 3: In some examples of the catheter of clause 1, the first end of the expandable member is a distal end and the second end of the expandable member is a proximal end.

Clause 4: In some examples of the catheter of any of clauses 1-3, the retainer defines a proximal portion and a distal portion, wherein the distal portion of the retainer is mechanically connected to the elongated body distal to the expandable member, and the proximal portion of the retainer is configured to overlap a distal portion of the expandable member and hold the expandable member in the collapsed configuration.

Clause 5: In some examples of the catheter of any of clauses 1-4, the retainer is expandable to release the second end of the expandable member to enable the expandable member to expand from the collapsed configuration to the expanded configuration.

Clause 6: In some examples of the catheter of clause 5, the retainer comprises a balloon.

Clause 7: In some examples of the catheter of clause 6, the elongated body defines a lumen and an outer wall defining at least one opening that fluidically connects the lumen and the balloon wherein the retainer is configured to expand when a fluid is introduced into the balloon via the lumen.

Clause 8: In some examples of the catheter of any of clauses 1-7, the elongated body comprises an inner member and an outer member, and the expandable member is mechanically connected to the outer member and the retainer is mechanically connected to the inner member, and longitudinal movement of the inner member relative to the outer member moves the retainer relative to the expandable member to release the second end of the expandable member from the retainer, and the expandable member is configured to expand from the collapsed configuration to the expanded configuration when the second end of the expandable member is released from the retainer.

Clause 9: In some examples of the catheter of any of clauses 1-8, the expandable member is configured to engage with a vessel wall of a patient when the expandable member is in the expanded configuration.

Clause 10: In some examples of the catheter of clause 9, when the vessel wall defines a curved shape and the expandable member is engaged with the vessel wall, the expandable member is configured to deflect a portion of the elongated body distal to the expandable member.

Clause 11: In some examples of the catheter of any of clauses 1-10, the expandable member defines a funnel in the expanded configuration.

Clause 12: In some examples of the catheter of clause 11, a mouth of the funnel faces a distal direction.

Clause 13: In some examples of the catheter of clause 11, a mouth of the funnel faces a proximal direction.

Clause 14: In some examples of the catheter of any of clauses 1-13, the catheter further comprises a layer of occlusive material attached to the expandable member, wherein the layer of occlusive material and the expandable member are configured to occlude blood flow within a vessel of a patient when the layer of occlusive material and the expandable member are in the expanded configuration.

Clause 15: In some examples of the catheter of clause 14, the layer of occlusive material comprises a polymer.

Clause 16: In some examples of the catheter of clause 14 or clause 15, the layer of occlusive material defines at least one opening configured to reduce air pockets in the expandable member when the expandable member is in the expanded configuration in blood flow of the patient.

Clause 17: In some examples of the catheter of any of clauses 1-16, the expandable member comprises a hydrophobic coating.

Clause 18: In some examples of the catheter of any of clauses 1-17, the expandable member is self-expandable.

Clause 19: In some examples of the catheter of clause 18, the self-expandable member comprises a shape-memory material.

Clause 20: In some examples, a method comprises introducing a catheter into a vasculature of a patient, the catheter comprising: an elongated body; an expandable member extending from a first end to a second end, the first end of the expandable member being mechanically connected to the elongated body, wherein the expandable member is configured to expand radially outward away from the elongated body from a collapsed configuration to an expanded configuration; and a retainer configured to overlap the second end of the expandable member to hold the expandable member in the collapsed configuration; and releasing the second end of the expandable member from the retainer such that the expandable member expands from the collapsed configuration to the expanded configuration.

Clause 21: In some examples of the method of clause 20, the first end of the expandable member is a proximal end and the second end of the expandable member is a distal end.

Clause 22: In some examples of the method of clause 20, the first end of the expandable member is a distal end and the second end of the expandable member is a proximal end.

Clause 23: In some examples of the method of any of clauses 20-22, the retainer defines a proximal portion and a distal portion, wherein the distal portion of the retainer is mechanically connected to the elongated body distal to the expandable member, and wherein the proximal portion of the retainer is configured to overlap a distal portion of the expandable member and hold the expandable member in the collapsed configuration.

Clause 24: In some examples of the method of any of clauses 20-23, the retainer is expandable to release the second end of the expandable member, and wherein releasing the second end of the expandable member from the retainer such that the expandable member expands from the collapsed configuration to the expanded configuration comprises expanding the retainer.

Clause 25: In some examples of the method of clause 24, the retainer comprises a balloon.

Clause 26: In some examples of the method of clause 25, the elongated body defines a lumen and an outer wall defining at least one opening that fluidically connects the lumen and the retainer, wherein the balloon is configured to expand when a fluid is introduced into the retainer via the lumen, and wherein expanding the retainer comprises introducing fluid into the balloon via the lumen.

Clause 27: In some examples of the method of any of clauses 20-26, the elongated body comprises an inner member and an outer member, and wherein the expandable member is mechanically connected to the outer member and the retainer is mechanically connected to the inner member, wherein releasing the second end of the expandable member from the retainer comprises longitudinally moving the inner member relative to the outer member to move the retainer relative to the expandable member to release the second end of the expandable member from the retainer.

Clause 28: In some examples of the method of any of clauses 20-27, the expandable member is configured to engage with a vessel wall of the vasculature of the patient when the expandable member is in the expanded configuration.

Clause 29: In some examples of the method of clause 28, the vessel wall defines a curved shape and when the expandable member is engaged with the vessel wall, the expandable member is configured to deflect a portion of the elongated body distal to the expandable member.

Clause 30: In some examples of the method of any of clauses 20-29, the expandable member defines a funnel in the expanded configuration.

Clause 31: In some examples of the method of clause 30, a mouth of the funnel faces a distal direction.

Clause 32: In some examples of the method of clause 30, a mouth of the funnel faces a proximal direction.

Clause 33: In some examples of the method of any of clauses 20-32, the catheter further comprises a layer of occlusive material attached to the expandable member, wherein the layer of occlusive material and the expandable member are configured to occlude blood flow within a vessel of a patient when the layer of occlusive material and the expandable member are in the expanded configuration.

Clause 34: In some examples of the method of clause 33, the layer of occlusive material comprises a polymer.

Clause 35: In some examples of the method of clause 33 or clause 34, the layer of occlusive material defines at least one opening configured to reduce air pockets in the expandable member when the expandable member is in the expanded configuration in blood flow of the patient.

Clause 36: In some examples of the method of any of clauses 20-35, the expandable member comprises a hydrophobic coating.

Clause 37: In some examples of the method of any of clauses 20-36, the expandable member is self-expandable.

Clause 38: In some examples of the method of clause 37, the self-expandable member comprises a shape-memory material.

Clause 39: In some examples, a catheter comprises an elongated body; an expandable member extending from a first end to a second end, the first end of the expandable member being mechanically connected to the elongated body and the second end of the expandable member being unconnected to the elongated body, wherein the expandable member is configured to expand radially outward away from the elongated body from a collapsed configuration to an expanded configuration, and wherein the expandable member defines a funnel in the expanded configuration; and a retainer configured to overlap only the second end to hold the expandable member in the collapsed configuration, wherein the retainer is configured to release the second end of the expandable member to enable the expandable member to expand from the collapsed configuration to the expanded configuration.

Clause 40: In some examples of the catheter of clause 39, the first end of the expandable member is a proximal end and the second end of the expandable member is a distal end.

Clause 41: In some examples of the catheter of clause 39, the first end of the expandable member is a distal end and the second end of the expandable member is a proximal end.

Clause 42: In some examples of the catheter of any of clauses 39-41, the retainer comprises a balloon.

Clause 43: In some examples of the catheter of clause 42, the elongated body defines a lumen and an outer wall defining at least one opening that fluidically connects the lumen and the retainer, wherein the balloon is configured to expand when a fluid is introduced into the retainer via the lumen.

Clause 44: In some examples of the catheter of any of clauses 39-43, the elongated body comprises an inner member and an outer member, and the expandable member is mechanically connected to the outer member and the retainer is mechanically connected to the inner member, and longitudinal movement of the inner member relative to the outer member moves the retainer relative to the expandable member to release the second end of the expandable member from the retainer.

Clause 45: In some examples of the catheter of clause 44, the inner member and the outer member are threadably connected and configured for rotational movement relative to one another, and wherein longitudinal movement of the inner member relative to the outer member is controllable by rotational movement of the inner member relative to the outer member.

Clause 46: In some examples of the catheter of any of clauses 39-45, the expandable member is configured to engage with a vessel wall of a patient when the expandable member is in the expanded configuration.

Clause 47: In some examples of the catheter of clause 46, when the vessel wall defines a curved shape and the expandable member is engaged with the vessel wall, the expandable member is configured to deflect a portion of the elongated body distal to the expandable member.

Clause 48: In some examples of the catheter of any of clauses 39-47, a mouth of the funnel faces a distal direction.

Clause 49: In some examples of the catheter of any of clauses 39-47, a mouth of the funnel faces a distal direction.

Clause 50: In some examples of the catheter of any of clauses 39-49, the catheter further comprises a layer of occlusive material attached to the expandable member, wherein the layer of occlusive material and the expandable member are configured to occlude blood flow within a vessel of a patient when the layer of occlusive material and the expandable member are in the expanded configuration.

Clause 51: In some examples of the catheter of clause 50, the layer of occlusive material comprises a polymer.

Clause 52: In some examples of the catheter of clause 50 or clause 51, the layer of occlusive material defines at least one opening configured to reduce air pockets in the expandable member when the expandable member is in the expanded configuration in blood flow of the patient.

Clause 53: In some examples of the catheter of any of clauses 39-52, the expandable member comprises a hydrophobic coating.

Clause 54: In some examples of the catheter of any of clauses 39-53, the expandable member comprises a radiopaque material.

Clause 55: In some examples of the catheter of any of clauses 39-54, the expandable member is self-expandable.

The details of one or more aspects of the disclosure are set forth in the accompanying drawings and the description below. Other features, objects, and advantages of the systems and techniques described in this disclosure will be apparent from the description and drawings, and from the claims.

DETAILED DESCRIPTION

Figure 1:
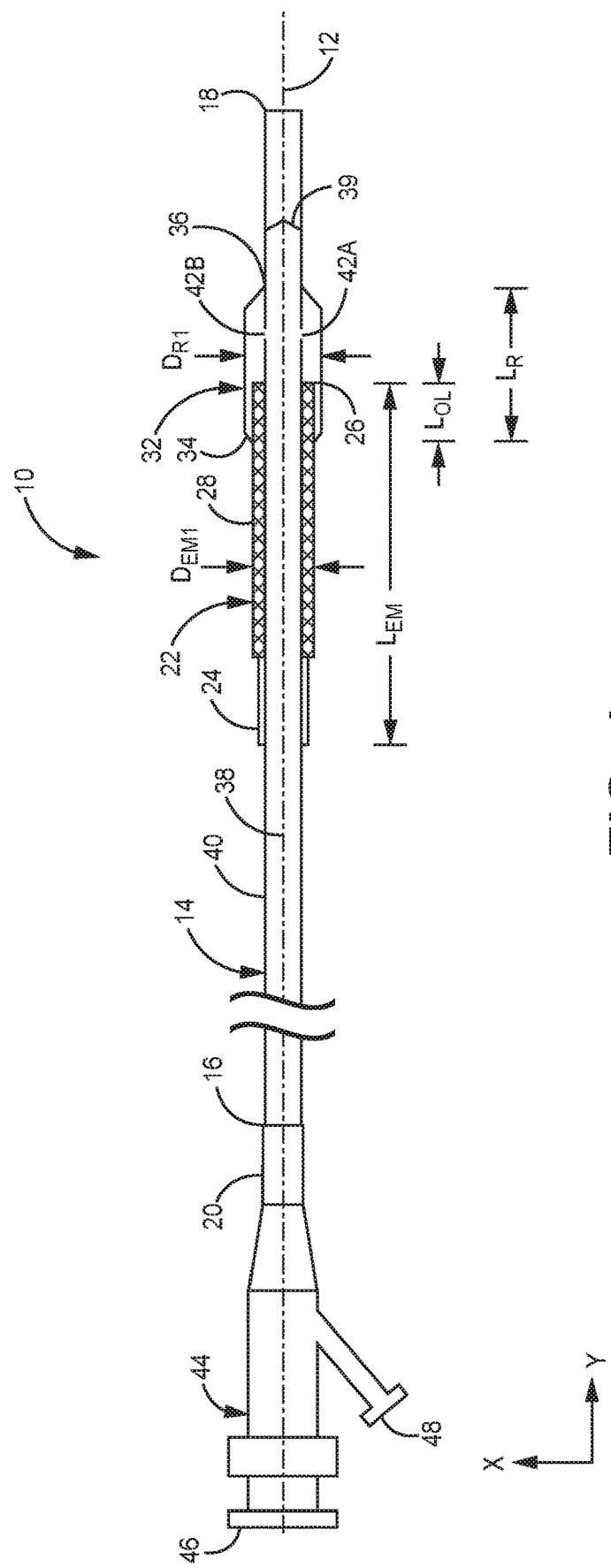
FIG. 1 is a schematic cross-sectional view of an example catheter including an elongated body and an expandable member held in a collapsed configuration by a retainer, where the cross-section is taken along a longitudinal axis of the catheter.

In examples described herein, a catheter includes an elongated body, an expandable member mechanically connected at a first end to the elongated body, and a retainer configured to releasably retain the expandable member in a collapsed configuration. Catheters as described herein may be configured for navigation through vasculature of a patient to facilitate the delivery of a therapeutic substance or a medical device to a target site within the patient, the aspiration of material from a blood vessel or other anatomical structure of a patient, and/or occlusion of a blood vessel of the patient. The expandable member of such catheters may be configured to expand radially outward away from the elongated body from the collapsed configuration to an expanded configuration when a second end of the expandable member (e.g., opposite the first end) is released by the retainer while the first end remains mechanically coupled to the elongated body.

An expandable member of a catheter described herein may act as a navigation structure that helps a user navigate the catheter through vasculature, e.g., by enabling deflection of the elongated body within vasculature when the expandable member is in the expanded configuration. As further described below, in some examples, an occlusive material may be connected to the expandable member. When the expandable member is expanded in these examples, the occlusive material may provide a flow barrier to reduce or prevent antegrade blood flow within a vessel and/or reduce or prevent retrograde flow of a fluid (e.g., an embolic substance) introduced into a target vessel, from the target vessel to an undesired location such as a feeding vessel.

The expandable members described herein may be configured to self-expand from a collapsed configuration to an expanded configuration. For example, the expandable member may be formed from a shape-memory material (e.g., Nitinol) in a stent-like or mesh-like configuration. In other examples, the expandable member may not necessarily be self-expandable and may be expanded with the aid of, for example, a balloon or another expandable structure.

The retainer may be configured to hold the expandable member in a collapsed configuration by overlapping the second end of the expandable member. In some examples, the retainer may be expandable to release the second end of the expandable member, thereby enabling the expandable member to expand from the collapsed configuration to the expanded configuration. In some such examples, the elongated body may define a lumen and an outer wall that defines at least one opening fluidically connecting the lumen and the retainer to enable an inflation fluid (e.g., saline) to be introduced into the retainer. An end of the retainer that does not overlap the second end of the expandable member (e.g., an end of the retainer furthest from the second end of the expandable member) may be mechanically coupled to the elongated body of the catheter. The retainer may be expandable to release the second end of the expandable member when an inflation fluid is introduced into the retainer via the lumen and the at least one opening. As the retainer expands, the retainer may move away from the expandable member such that the retainer does not overlap the second end of the expandable member, thereby releasing the expandable member and enabling the expandable member to expand radially outward from the elongated body from the collapsed configuration to the expanded configuration. In the expanded state, the first end of the expandable member may remain connected to the elongated member while the second end of the expandable member is spaced from the elongated member in a radial direction.

In other examples, the retainer can be configured to release the second end of the expandable member using another technique. For example, the elongated body may include an inner member and an outer member, and the expandable member may be mechanically connected to the outer member and the retainer may be mechanically connected to the inner member. Longitudinal movement of the inner member relative to the outer member moves the retainer relative to the expandable member, thereby releasing the second end of the expandable member from the retainer and enabling the expandable member to expand from the collapsed configuration to the expanded configuration. In these examples, the retainer may not be expandable.

In any such examples, the expandable member may be configured to engage with a vessel wall of a patient when the expandable member is in the expanded configuration, which may help a clinician navigate the catheter through vasculature by deflecting the elongated body when the expandable member is in the expanded configuration. For example, contact between the expandable member and the vessel wall may enable deflection of the elongated body during navigation of the catheter through the vasculature to a treatment site when a distal (i.e., leading) portion of the catheter encounters a curved portion of the vessel. As an example, a clinician may advance the catheter through a blood vessel until the expandable member is positioned within the curved portion of the vessel or proximal to the curved portion. The clinician then may release the second end of the expandable member from the retainer to expand the expandable member, such as by expanding the retainer or moving an inner member of the elongated body to move the retainer relative to the expandable member and release the second end of the expandable member from the retainer. The expandable member expands into contact with the curved portion of the vessel, and contact between the expandable member and the curved portion of the vessel may cause deflection of a portion of the elongated body distal to the expandable member into a curved or bent configuration that better approximates the curved shape of the vessel than a straight elongated body configuration. With the elongated body in such a curved or bent configuration, the clinician may advance the elongated body through the curved portion of the vessel more readily relative to when the elongated body is in a linear configuration.

In some examples, the catheter further may include a layer of occlusive material that is attached to the expandable member and configured to at least partially cover (e.g., fully cover or partially cover) the expandable member when the expandable member is in the expanded configuration. The occlusive material may be a flexible, substantially fluid-impermeable (e.g., fluid impermeable but for weep holes that are configured to help prevent air pockets) material such as a polymer. The expandable member and the layer of occlusive material together may help prevent retrograde flow of a substance (e.g., an embolic substance) introduced into a vessel during a medical procedure past the expandable member and/or may provide a temporary vessel-occlusion device by reducing or preventing antegrade blood flow. For example, the layer of occlusive material and the expandable member may be configured to reduce or prevent antegrade blood flow within a vessel of a patient when the layer of occlusive material and the expandable member are in the expanded configuration and the expandable member is engaged with a vessel wall. In some examples, the expandable member may define a funnel shape when in the expanded configuration, with a mouth of the funnel facing in either a proximal or a distal direction relative to the elongated body. Regardless of the direction a mouth of such a funnel, the retainer may be configured to overlap the end of the expandable member that defines the funnel when the retainer is holding the expandable member in the collapsed configuration.

The retainers described herein may reduce or eliminate a need to include an additional sheath in a catheter to retain an expandable member in a collapsed configuration, thereby enabling an elongated body of a catheter to have a relatively larger diameter relative to other example catheters in which an additional sheath is used to retain an expandable member. Thus, the example retainers described herein may enable an elongated body of a catheter to define a relatively larger working channel that may be used in a medical procedure, such as for aspiration of a fluid and/or delivery of a medical device or fluid.

Other proposed methods of preventing retrograde flow of embolic substance from a target vessel into a primary feeding vessel include first casting a liquid embolic substance to form a plug at a tip of a delivery catheter and then delivering additional embolic substance to fill the target vessel. This process may reduce or prevent retrograde flow of the embolic substance but may be relatively time consuming compared to the use of an expandable member and occlusive material described herein. In other examples, a dual-lumen balloon may be used as a backstop while injecting an embolic substance into the target vessel. This option also may reduce or prevent retrograde flow but can add complexity to the procedure and may involve a possibility of balloon rupture due to over-inflation of the balloon.

This disclosure describes examples of catheters having expandable members that may function as a backstop and/or steering member to help increase the efficiency and/or improve clinical outcomes of vascular treatment procedures. For example, an expandable member and layer of occlusive material, as described herein, may reduce the amount of time needed to treat a vessel with an embolic substance by reducing or eliminating need for casting a plug of embolic substance at a tip of a delivery catheter, and/or reducing or eliminating need for a balloon backstop. Additionally, or alternatively, the steerability provided to the catheter by an expandable member and a retaining member, as described herein, may reduce the amount of time needed to navigate the catheter through curved portions of the patient's vasculature to reach a target vessel. Thus, the example catheters described herein may provide one or more benefits over other catheters that may be used in vascular procedures.

While the present disclosure describes catheters primarily in the context of procedures for treating vascular conditions such as arteriovenous malformations (AVMs), the devices of the present disclosure may also be used in procedures to treat other vascular conditions or to access portions of a patient's vasculature for other purposes. For example, the catheters described herein may be used as temporary vessel occlusion devices for use in ischemic stroke interventional procedures (such as clot aspiration procedures or stentriever thrombectomy procedures) or as a backstop device during other neuro-interventional procedures.

Figure 2:
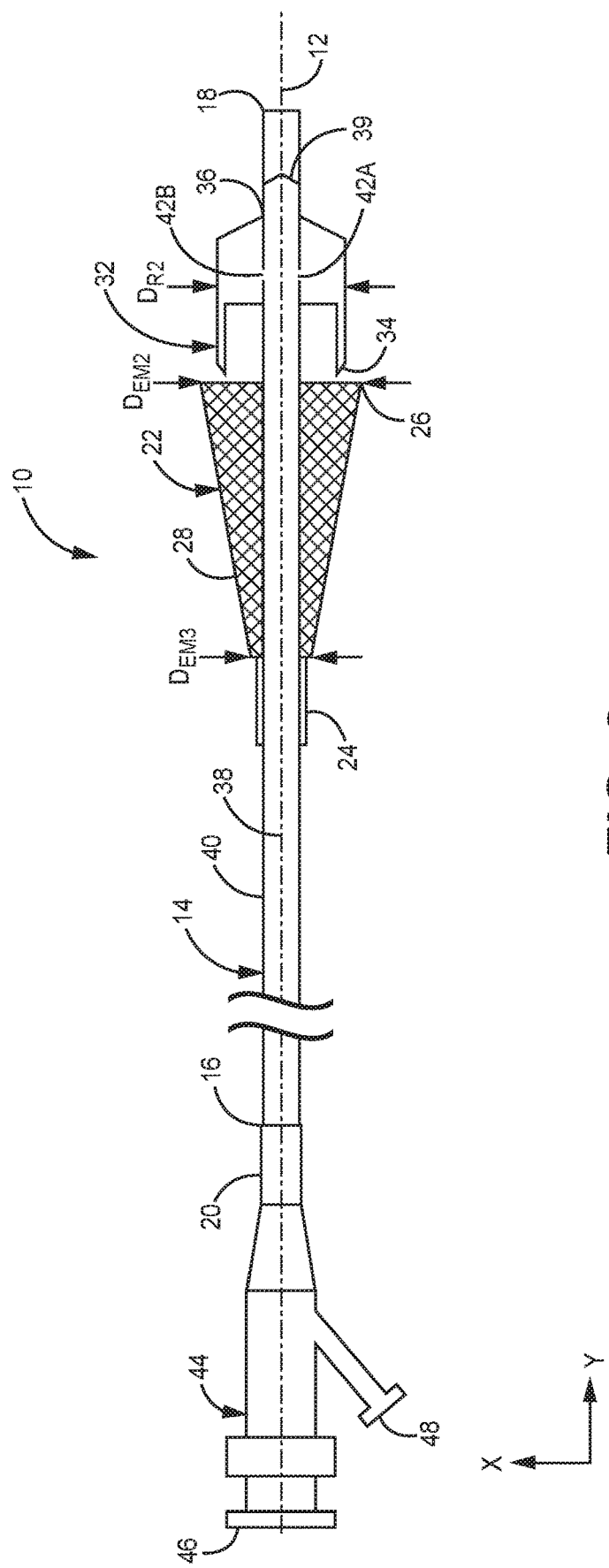
FIG. 2 is a schematic cross-sectional view of the catheter of FIG. 1 with the expandable member in an expanded configuration and released from the retainer, where the cross-section is taken along the longitudinal axis of the catheter.

FIGS. 1 and 2 illustrate an example catheter 10, which is configured to be navigated through vasculature of a patient and defines one or more lumens that facilitate the delivery of a therapeutic substance or a medical device to a target site within the patient, aspiration of material from a blood vessel or other part of a patient, and/or occlusion of a blood vessel of the patient. FIG. 1 is a schematic cross-sectional view of catheter 10, where the cross-section is taken along a longitudinal axis 12 of catheter 10. Longitudinal axis 12 may be a central longitudinal axis of one or more components of catheter 10, such as an elongated body 14 of catheter 10.

Elongated body 14 of catheter 10 extends from a proximal end 16 to a distal end 18. In some examples, catheter 10 may include a strain relief member 20. In such examples, proximal end 16 of elongated body 14 may be partially covered by strain relief member 20, such that proximal end 16 of elongated body 14 may be more proximal than as shown in FIG. 1. Catheter 10 further includes an expandable member 22 that extends from a first (e.g., proximal) end 24 to a second (e.g., distal) end 26. In the example of FIGS. 1 and 2, first end 24 of expandable member 22 is mechanically coupled to elongated body 14 either directly or indirectly (e.g., with a sleeve or another material positioned between first end 24 and elongated body 14). For example, first end 24 of expandable member 22 may be bonded, crimped, swaged, welded, or otherwise secured to elongated body 14. In FIG. 1, expandable member 22 is in a collapsed configuration, in which expandable member 22 may be folded or rolled into a physically smaller radial profile than an expanded configuration of expandable member 22 illustrated in FIG. 2. The general shape of the collapsed configuration of expandable member 22 shown in FIG. 1 is intended to be illustrative and not limiting. Other shapes and configurations of the collapsed configuration of expandable member 22 are also possible.

Dimensions of expandable member 22 and/or one or more other components of catheter 10 may be selected based on dimensions of one or more vessels of the patient. Expandable member 22 has a length "$L_{EM}$" (measured parallel to longitudinal axis 12) and a collapsed expandable member diameter "$D_{EM1}$" measured orthogonal to longitudinal axis 12 when expandable member 22 is in the collapsed configuration. Length $L_{EM}$ and diameter $D_{EM1}$ may be selected based on the desired properties for catheter 10. In some examples, length $L_{EM}$ of expandable member 22 may be from about 1 millimeters millimeter (mm) to about 7 mm and collapsed expandable-member diameter $D_{EM1}$ may be from about 0.5 mm to about 2.0 mm. Although $D_{EM1}$ is described herein as being a diameter of expandable member 22, in some examples, expandable member 22 may have a non-circular cross-sectional shape in the collapsed and/or expanded configurations in other examples. $D_{EM1}$ may be any greatest dimension of expandable member 22 measured orthogonal to longitudinal axis 12 when expandable member 22 is in the collapsed configuration.

Expandable member 22 has any suitable configuration that enables it to be collapsed into a low-profile configuration for delivery and navigation through vasculature of a patient, and expand radially outward from collapsed diameter $D_{EM1}$ to an expanded configuration (e.g., as shown in FIG. 2) in which expandable member 22 may engage with a vessel wall of a patient, such as a target vessel to which a clinician may navigate catheter 10. In the example shown in FIG. 1, expandable member 22 may include a plurality of struts 28. Struts 28 may define any suitable pattern and cell structure (e.g., open cells or closed cells), such as a serpentine, zig-zag, or accordion-like pattern. In other examples, struts 28 of expandable member 22 may have other configurations, such as one or more compressible coils. In other examples, expandable member 22 may include an expandable mesh material. In any such examples, expandable member 22 may be self-expandable (e.g., formed from nitinol or another shape-memory material).

In some examples, expandable member 22 may include a hydrophobic coating or a lubricious coating on one or more outer surfaces defined by expandable member 22, which may help reduce or prevent sticking of expandable member 22 to some substances that may be delivered during a vascular interventional procedure, such as some embolic substances. In some examples, one or more components of expandable member 22 (e.g., struts 28) may include markers, coatings, or jackets, formed from a material that may be visualized during fluoroscopy, such as platinum, or another suitable radiopaque material.

Catheter 10 further includes an expandable retainer 32 including a proximal portion 34 and a distal portion 36 distal to proximal portion 34. In some examples, distal portion 36 of expandable retainer 32 is mechanically connected to elongated body 14 distal to second end 26 of expandable member 22, such as by bonding, crimping, swaging, welding, or otherwise securing distal portion 36 of expandable retainer 32 to elongated body 14. In FIG. 1, expandable retainer 32 is in a collapsed configuration, in which expandable retainer 32 may be folded or rolled into a physically smaller profile than when in an expanded configuration illustrated in FIG. 2. The general shape of the collapsed configuration of expandable retainer 32 shown in FIG. 1 is intended to be illustrative and not limiting. Other shapes and configurations of the collapsed configuration of expandable retainer 32 are also possible.

Expandable retainer 32 is configured to overlap second end 26 of expandable member 22 and retain expandable member 22 in the collapsed configuration, as illustrated in FIG. 1. For example, proximal portion 34 of expandable retainer 32 may be configured to overlap a distal portion of expandable member 22 that includes second end 26 of expandable member 22. Proximal portion 34 may have an overlap length "$L_{OL}$" that defines the portion of expandable retainer 32 that overlaps expandable member 22. In some examples, a ratio of overlap length $L_{OL}$ to length $L_{EM}$ of expandable member 22 may be about 1:2, 1:3, 1:4 or 1:5. However, the extent to which proximal portion 34 overlaps expandable member 22 may vary in other examples.

In the example shown in FIGS. 1 and 2, expandable retainer 32 is configured to expand radially outward from the collapsed configuration illustrated in FIG. 1 to the expanded configuration illustrated in FIG. 2. Expandable retainer 32 has a length "$L_R$" (measured parallel to longitudinal axis 12 when expandable retainer 32 is in the collapsed configuration) and a collapsed retainer diameter "$D_{R1}$" (measured orthogonal to longitudinal axis 12) when retainer 32 is in the collapsed configuration. Length $L_R$ may be from about 10 mm to about 30 mm. Collapsed retainer diameter $D_{R1}$ may be from about 0.6 mm to about 2.2 mm. Although $D_{R1}$ is described herein as being a diameter of expandable retainer 32, in some examples, expandable retainer 32 may have a non-circular cross-sectional shape, such that $D_{R1}$ may be any greatest dimension of expandable retainer 32 measured orthogonal to longitudinal axis 12 when expandable retainer 32 is in the collapsed configuration. For example, proximal portion 34 of expandable retainer 32, which overlaps the distal portion of expandable member 22 that includes second end 26, may have a non-circular cross-sectional shape.

In some examples, proximal portion 34 of expandable retainer 32 may comprise two or more tabs defining spaces therebetween. The force with which expandable retainer 32 retains expandable member 22 in the collapsed configuration may be varied by varying the dimensions or number of the tabs of proximal portion 34 and/or the spaces defined by the tabs of proximal portion 34. In other examples, expandable retainer 32 may be configured as a balloon.

Elongated body 14 defines a lumen 38, an optional valve 39, and an outer wall 40. In examples in which distal end 18 of elongated body 14 defines an opening, elongated body 14 may include valve 39, which is configured to block the flow of inflation fluid introduced into lumen 38 from exiting distal end 18 of elongated body 14. Valve 39 may extend radially inward from outer wall 40 into lumen 38. In other examples, elongated body 14 may define one or more additional lumens (not shown) in addition to lumen 38. Such additional lumens may be used to aspirate fluid and/or deliver a drug or medical agent to a vessel. In such examples, lumen 38 may be an inflation lumen that does not define a distal opening and, therefore, may not include valve 39. Outer wall 40 may define at least one opening that fluidically connects lumen 38 and expandable retainer 32. For example, outer wall 40 may define two openings, 42A and 42B, as illustrated in FIG. 1. In some examples, catheter 10 further may include a hub 44 positioned at proximal end 16 of elongated body 14. In such examples, lumen 38 may extend longitudinally through elongated body 14 at least from openings 42A, 42B to hub 44. Hub 44 may include at least one of a first port 46 or a second port 48, one or both of which may be in fluid communication with lumen 38. Lumen 38 is configured to receive a fluid that is introduced into the lumen 38 via hub 44 to expand or inflate expandable retainer 32 (e.g., once catheter 10 has been navigated to a target site in the vessel).

Expandable retainer 32 may be formed from any suitable material that provides sufficient strength and flexibility to withstand the pressures exerted on expandable retainer 32 during a medical procedure. The materials from which the expandable retainer 32 is formed may be biocompatible with patient tissue. In some examples, materials from which expandable retainer 32 is formed may include nylon, polyethylene terephthalate (PET), polyethylene (such as cross-linked polyethylene), expanded polytetrafluoroethylene (ePTFE), polyurethane, polyvinyl chloride, silicone elastomer, or the like. The material of expandable retainer 32 may have sufficient elasticity to enable expandable retainer 32 to expand to the expanded configuration and thereafter to collapse to a smaller diameter (e.g., substantially to collapsed retainer diameter $D_{R1}$) when the fluid used to expand expandable retainer 32 is aspirated from expandable retainer 32 or otherwise exits expandable retainer 32. For example, fluid used to expand expandable retainer 32 may be aspirated from expandable retainer 32 after expanding expandable member 22 to deflect a portion of elongated body 14 distal to expandable member 22 and prior to continuing to advance catheter 10 to a treatment site and/or prior to aspirating a portion of catheter 10 including expandable retainer 32 into an outer sheath (not shown). Expandable retainer 32 may be made by any suitable technique, such as by molding, or extrusion, or other manufacturing techniques.

FIG. 2 is a schematic cross-sectional view of catheter 10 of FIG. 1 with expandable member 22 in the expanded configuration and released from expandable retainer 32, where the cross-section is taken along longitudinal axis 12 of catheter 10. FIG. 2 illustrates catheter 10 after a fluid has been introduced into expandable retainer 32, via lumen 38 and openings 42A, 42B, to expand expandable retainer 32. As expandable retainer 32 expands, a diameter of expandable retainer 32 increases from collapsed expandable-retainer diameter $D_{R1}$ to a larger expanded retainer diameter "$D_{R2}$" of the expanded configuration of expandable retainer 32. Larger expanded retainer diameter $D_{R2}$ may be from about 0.6 mm to about 3.0 mm. Thus, larger expanded retainer diameter $D_{R2}$ may be smaller than a larger expandable member diameter"$D_{EM2}$." As expandable retainer 32 expands, the proximal portion of expandable retainer 32 that overlaps second end 26 of expandable member 22 releases second end 26, which enables expandable member 22 to expand radially outward (e.g., self-expand) from the collapsed configuration illustrated in FIG. 1 to the expanded configuration illustrated in FIG. 2. Additionally, or alternatively, expandable member 22 may be expandable via actuation of a push/pull wire attached to expandable member 22 (not shown), or any other suitable feature configured to expand and/or collapse expandable member 22.

In the expanded configuration, expandable member 22 defines a larger expandable-member diameter "$D_{EM2}$" compared to the collapsed expandable-member diameter $D_{EM1}$. Expandable member 22 may define diameter $D_{EM2}$ at least at second end 26 of expandable member 22. Expandable-member diameter $D_{EM2}$ may be from about 2.5 mm to about 8.0 mm. In some examples, expandable member diameter $D_{EM2}$ may correspond to an inner diameter of a vessel of a patient into which catheter 10 may be introduced, as self-expansion of expandable member 22 within a lumen defined by the vessel of the patient may bring expandable member 22 into contact with an inner surface of the vessel. Because expanded retainer diameter $D_{R2}$ of expandable retainer 32 may be smaller than larger expandable-member diameter $D_{EM2}$, expandable retainer 32 is not necessarily configured to contact the inner surface of the vessel when expandable retainer 32 is in the expanded configuration. In this manner, the configuration of expandable retainer 32 advantageously may reduce or eliminate a possibility of vessel rupture due to over-inflation of the balloon against an inner surface defined by the vessel.

Additionally, or alternatively, expandable retainer 32 may reduce or eliminate a need to include an additional sheath in catheter 10 to retain expandable member 22 in the collapsed configuration. In this manner, expandable retainer 32 may enable elongated body 14 to define a relatively larger diameter for a given target vessel, thereby enlarging lumen 38 (e.g., relative to other catheters that may include an additional sheath). Thus, lumen 38 may define a relatively larger working channel that may be used in a medical procedure using catheter 10.

Figure 9A:
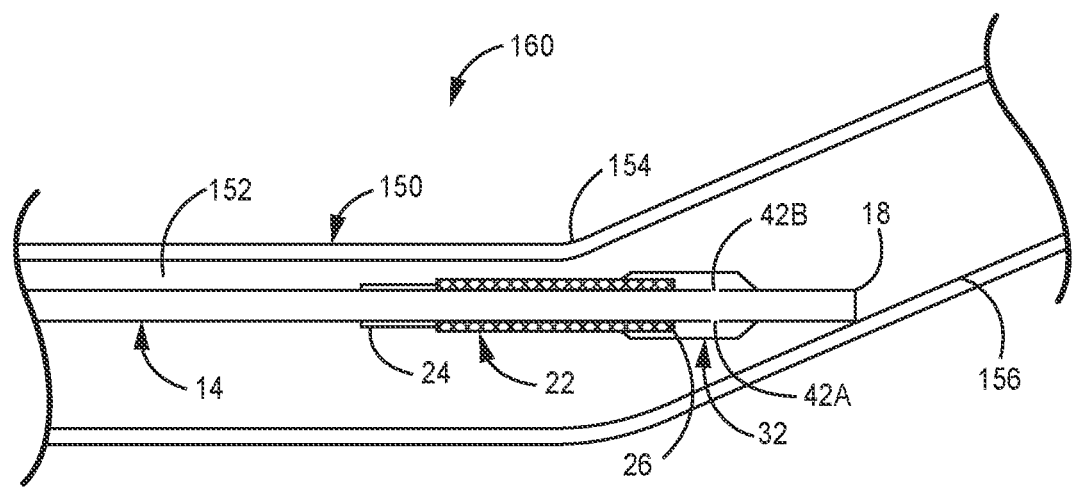
FIGS. 9A and 9B are a series of side views showing an example catheter being operated in accordance with the technique described with respect to FIG. 8.
Figure 9B:
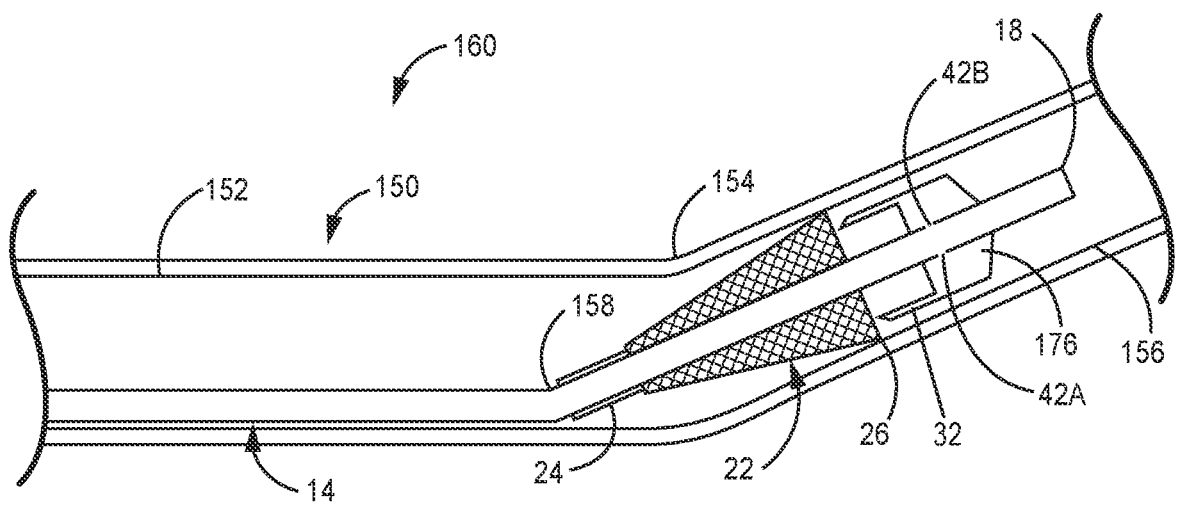

Expandable member 22 may contact and engage with the inner surface of the vessel (e.g., as shown in FIG. 9B and described with respect thereto) when in an expanded state, which may cause a portion of elongated body 14 distal to first end 24 of expandable member 22 to deflect relative to a central longitudinal axis of a more proximal portion of elongated body 14. Thus, at least a portion of elongated body 14 distal to expandable member 22 may better conform to a curved shape of a vessel of a patient, deflect to better center itself within the vessel, and/or pivot within the vessel when expandable member 22 is in the expanded configuration. In this manner, expandable member 22 may help a user navigate catheter 10 through vasculature by enabling deflection of elongated body 14 when expandable member 22 is expanded from the collapsed configuration to the expanded configuration at a curved portion of a vessel through which catheter 10 is navigated, as further described below with respect to FIGS. 9A and 9B.

The presence of expandable member 22 on elongated body 14 may increase the flexural stiffness of catheter 10 at that location on elongated body 14. Connecting first end 24 of expandable member 22 to elongated body 14 closer to proximal end 16 of elongated body 14 than distal end 18 may enable a distal portion (distal to expandable member 22) of elongated body 14 to be more flexible yet still aid navigation of elongated body 14 into distal vasculatures.

In some examples, second end 26 of expandable member 22 may be about 10 mm to about 80 mm proximal to distal end 18 of elongated body 14, although second end 26 of expandable member 22 may be positioned closer to distal end 18 or further from distal end 18 in other examples. For example, second end 26 of expandable member 22 may be more than about 10 mm to about 40 mm proximal to distal end 18 of elongated body 14 when blocking antegrade blood flow toward a captured clot during a medical procedure using A Direct Aspiration first Pass Technique (ADAPT) for acute stroke thrombectomy, or any other aspiration or removal of thrombus or other material from the neurovasculature or other blood vessels. The clot may be suctioned at distal end 18 of elongated body 14, and blocking antegrade blood flow toward the captured clot may help prevent antegrade blood flow from breaking up the captured clot or opposing or disrupting the suction applied to the clot. In this manner, restriction of blood flow provided relatively closer to proximal end 16 of elongated body 14 may improve an outcome of an aspiration procedure in which blocking antegrade blood flow may be desirable. In some such examples, expandable member 22 may remain in the expanded configuration until at least a portion of catheter 10 including expandable member 22 is aspirated into an outer sheath (not shown).

As illustrated in FIG. 2, in some examples, expandable member 22 may define a funnel shape when in the expanded configuration. The funnel shape may help expandable member 22 reduce retrograde flow of a substance (e.g., an embolic substance) through vasculature (e.g., into a parent vessel) when in the expanded configuration by providing a framework to which occlusive material (not shown) may attach, which in combination with expandable member 22 may prevent backflow of the introduced substance. Examples of occlusive material that may be attached to expandable member 22 are discussed below with respect to FIGS. 7A and 7B.

In examples in which expandable member 22 defines a funnel shape, a diameter of expandable member 22 may taper from expanded diameter $D_{EM2}$ at second end 26 of expandable member 22 to a diameter "$D_{EM3}$" at first end 24 of expandable member 22, such that a mouth of the funnel defined by expandable member 22 faces a distal direction (e.g., toward distal end 18 of elongated body 14). Diameter $D_{EM3}$ may be substantially similar to diameter $D_{EM1}$ of expandable member 22 when expandable member 22 is in the collapsed configuration. That is, in some examples in which expandable member 22 defines a funnel shape when in the expanded configuration, a proximal portion of expandable member 22 that includes first end 24 may not expand substantially from $D_{EM1}$, although the dimensions of expandable member 22 may be adapted to dimensions of a target vessel or a technique in which catheter 10 may be used.

Additionally, or alternatively, a mouth of a funnel defined by expandable member 22 that faces in a distal direction, as shown in FIGS. 1 and 2, may enable expandable member 22 to reduce or prevent pooling of blood within expandable member 22 during a procedure in which expandable member acts as a backstop against retrograde flow of a substance introduced into a target vessel. For example, catheter 10 may further include a layer of occlusive material (not shown), which may be formed of a substantially fluid-impermeable (e.g., fluid impermeable but for weep holes that are configured to help prevent air pockets) material and which in combination with expandable member 22 may prevent backflow of a substance (e.g., an embolic substance) introduced into a target vessel to reduce or prevent retrograde flow of the introduced substance from the target vessel into a parent vessel that may be located proximal of expandable member 22. Catheter 10 may be introduced into a vessel of a patient with the flow of blood, such that blood flows from first end 24 of expandable member 22 toward second end 26 of expandable member 22. Thus, connecting first end 24 of expandable member 22 to elongated body 14 such that a mouth of a funnel defined by expandable member 22 when expandable member 22 is in the expanded configuration may enable blood to flow against expandable member 22 substantially without pooling within expandable member 22. In some examples, reducing or eliminating pooling of blood within an expandable member configured to temporarily occlude the vessel may provide one or more advantages. For example, pooling of blood may cause stasis that can initiate a clotting cascade that can later embolize when withdrawing catheter 10 into an outer sheath for withdrawal from the patient.

Figure 3:
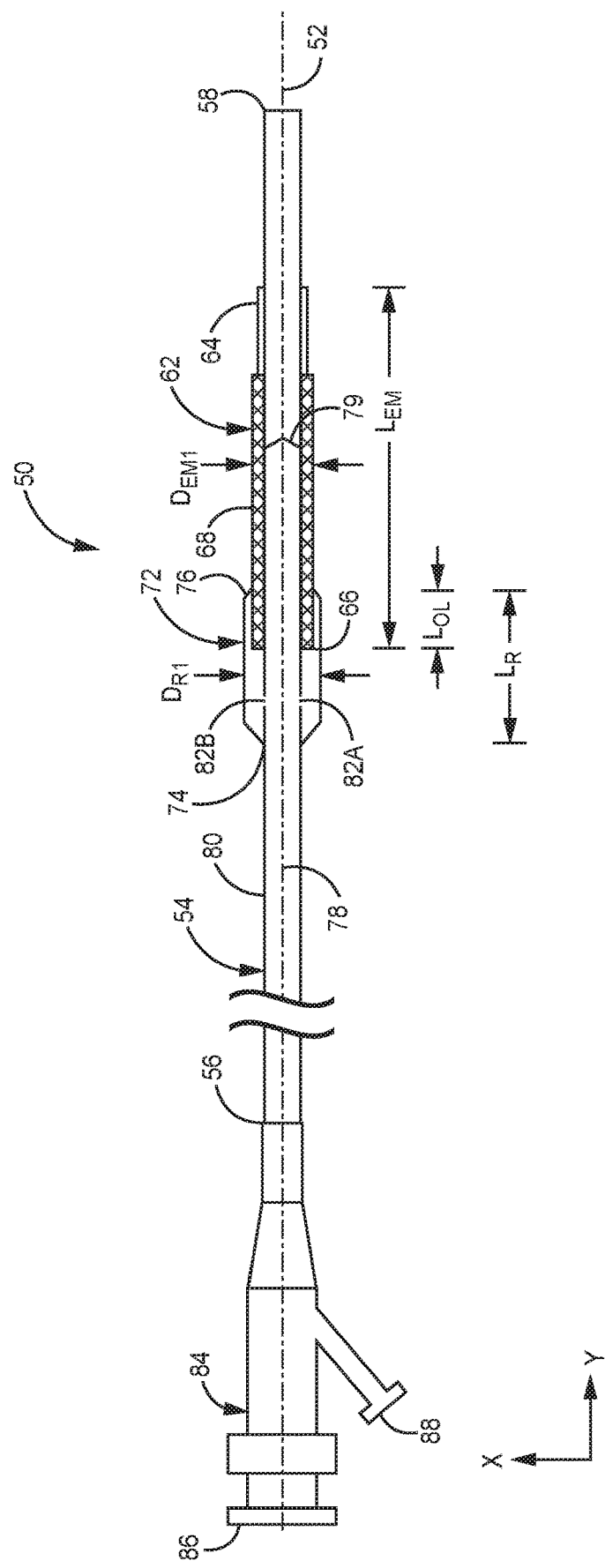
FIG. 3 is a schematic cross-sectional view of another example catheter including an elongated body and an expandable member held in a collapsed configuration by a retainer, where the cross-section is taken along a longitudinal axis of the catheter.
Figure 4:
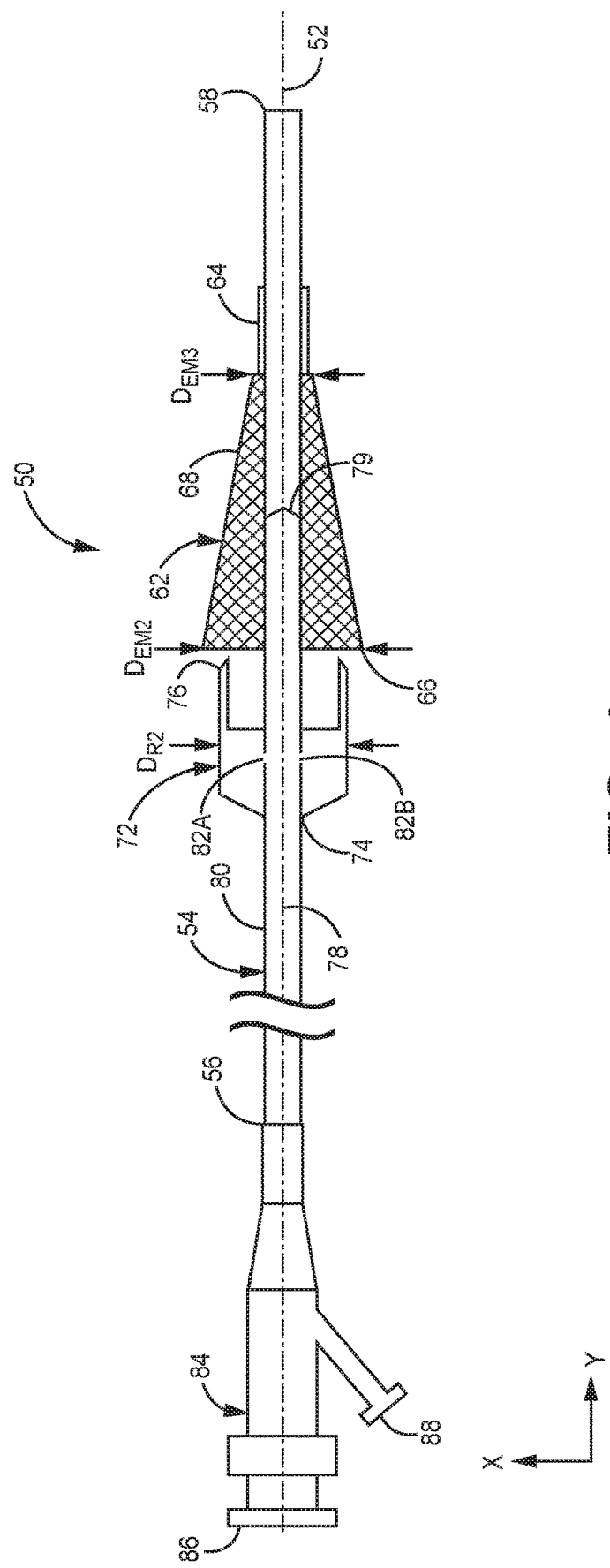
FIG. 4 is a schematic cross-sectional view of the catheter of FIG. 3 with the expandable member in an expanded configuration and released from the retainer, where the cross-section is taken along the longitudinal axis of the catheter.

FIGS. 3 and 4 illustrate another example catheter 50 that includes an expandable member 62 and a retainer 72 configured to hold the expandable member in a collapsed configuration. Catheter 50 is similar to catheter 10 shown in FIGS. 1 and 2, except that the expandable member 62 faces in an opposite direction than expandable member 22 of catheter 10. FIGS. 3 and 4 are schematic cross-sectional views of catheter 50, where the cross-section is taken along a longitudinal axis 52 of catheter 50. Longitudinal axis 52 may be a central longitudinal axis of one or more components of catheter 50, such as an elongated body 54 of catheter 50.

Elongated body 54 of catheter 50 extends from a proximal end 56 to a distal end 58. Catheter 50 further includes an expandable member 62 that extends from a first (e.g., distal) end 64 to a second (e.g., proximal) end 66. In the example of FIGS. 3 and 4, first end 64 of expandable member 62 is mechanically coupled to elongated body 54 either directly or indirectly (e.g., with a sleeve or another material positioned between first end 64 and elongated body 54). For example, first end 64 of expandable member 62 may be bonded, crimped, swaged, welded, or otherwise secured to elongated body 54. Expandable member 62 can be generally similar to expandable member 22 and may include a plurality of struts 68 or an expandable mesh material. As illustrated in FIG. 4, expandable member 62 may be expandable from collapsed diameter $D_{EM1}$ to the expanded configuration in which expandable member 62 may engage with a vessel wall of a patient, such as a target vessel to which a clinician may navigate catheter 50.

Catheter 50 further includes an expandable retainer 72 extending from a proximal portion 74 to a distal portion 76. Expandable retainer 72 can be generally similar to expandable retainer 32, except expandable retainer 72 can be configured to retain a proximal end of an expandable member 62. In some examples, proximal portion 74 of expandable retainer 72 is mechanically connected to elongated body 54 proximal to second end 66 of expandable member 62, such as by bonding, crimping, swaging, welding, or otherwise securing proximal portion 74 of expandable retainer 72 to elongated body 54. Distal portion 76 of expandable retainer 72 is configured to overlap second end 66 of expandable member 62 and retain expandable member 62 in the collapsed configuration, as illustrated in FIG. 3. For example, distal portion 76 of expandable retainer 72 is configured to overlap a proximal portion of expandable member 62 that includes second end 66 of expandable member 62. Distal portion 76 may have an overlap length "$L_{oL}$" that defines the portion of expandable retainer 72 that overlaps expandable member 62.

Elongated body 54 defines a lumen 78, a valve 79, and an outer wall 80. In examples in which distal end 58 of elongated body 54 defines an opening, elongated body 54 may include valve 79, which may extend radially inward from outer wall 80 into lumen 78. In such examples, valve 79 may help prevent inflation fluid introduced into lumen 78 from exiting distal end 58 of elongated body 54. In other examples, elongated body 54 may define one or more additional lumens (not shown) in addition to lumen 78. Such additional lumens may be used to aspirate fluid and/or deliver a drug or medical agent to a vessel. In such examples, lumen 78 may not necessarily define a distal opening and may not necessarily include valve 79. Outer wall 80 may define at least one opening that fluidically connects lumen 78 and expandable retainer 62. For example, outer wall 80 may define two openings, 82A and 82B, as illustrated in FIG. 3. In some examples, catheter 50 further may include a hub 84 positioned at proximal end 56 of elongated body 54. Hub 84 may include at least one of a first port 86 or a second port 88, one or both of which may be in fluid communication with lumen 78.

FIG. 4 is a schematic cross-sectional view of catheter 50 of FIG. 3 with expandable member 62 in the expanded configuration and released from expandable retainer 72, where the cross-section is taken along longitudinal axis 52 of catheter 50. FIG. 4 illustrates catheter 50 after a fluid has been introduced into expandable retainer 72, via lumen 78 and openings 82A, 82B, to expand expandable retainer 72 radially outward. As expandable retainer 72 releases second end 66 of expandable member 62, expandable member 62 expands radially outward from the collapsed configuration illustrated in FIG. 3 to the expanded configuration illustrated in FIG. 4 while first end 64 remains mechanically coupled to elongated body 54.

One or more features of catheter 50 of FIGS. 3 and 4 may be substantially similar to the corresponding features of catheter 10 described above with respect to FIGS. 1 and 2 and will not be discussed again in detail here. For example, elongated body 54, expandable member 62, expandable retainer 72, and hub 84 may be substantially similar to elongated body 14, expandable member 22, expandable retainer 32, and hub 44 of catheter 10, respectively. As another example, distal portion 76 of expandable retainer 72 is configured to release second end 66 of expandable member 62 when a fluid has been introduced, via lumen 78 and openings 82A, 82B, to expand expandable retainer 72 to the expanded configuration illustrated in FIG. 4, in a manner substantially similar to the manner in which expandable retainer 32 is configured to release second end 26 of expandable member 22. As with catheter 10, a ratio of overlap length $L_{oL}$ of distal portion 76 of expandable retainer 72 to length $L_{EM}$ of expandable member 62 may be about 1:2, 1:3, 1:4 or 1:5, although the extent to which distal portion 76 of expandable retainer 72 overlaps expandable member 62 may vary in other examples.

Catheter 50 may differ from catheter 10 in that first end 64 of expandable member 62, which is mechanically connected to elongated body 54, is distal to second end 66 of expandable member 62 instead of being proximal to second end 66. Catheter 50 further may differ from catheter 10 in that distal portion 76 of expandable retainer 72 is configured to overlap first end 64 of expandable member 62 instead of proximal portion 74 being configured to overlap first end 64 of expandable member 62 when expandable member 62 is retained by expandable retainer 72 in the collapsed configuration. Thus, distal portion 76 of expandable retainer 72 may comprise two or more tabs defining spaces therebetween, as described above with respect to proximal portion 34 of expandable retainer 32. Thus, in examples in which expandable member 62 defines a funnel shape when expandable member 62 is in the expanded configuration, as illustrated in FIG. 4, catheter 50 may further differ from catheter 10 in that expandable member 62 defines a funnel shape in which a mouth of the funnel faces a proximal direction (e.g., toward proximal end 56 of elongated body 54) instead of a distal direction.

Expandable member 62 that defines a funnel shape having a mouth facing in a proximal direction may, in some examples, enable the use of antegrade flow of blood to help expand expandable member 62, such that expandable member 62 does not need a lot of radial outward force to expand. Reducing the amount of radially outward force needed to expand expandable member 62 may enable expandable member 62 (or at least the expandable structures of expandable member 62) to be thinner, which may reduce the overall profile of expandable member 62. A lower profile expandable member 62 may further facilitate navigation of catheter 50 to certain target sites within the vasculature of a patient.

In some other examples, a retainer may be disengaged from an expandable member to permit the expandable member to expand using techniques other than inflation of an expandable retainer via introduction of an inflation fluid via a lumen defined by an elongated body, as described above with respect to the examples of catheter 10 of FIGS. 1 and 2 and catheter 50 of FIGS. 3 and 4. For example, a retainer may be disengaged from an end of an expandable member via relative longitudinal movement of two portions of an elongated body of a catheter, one of which may be mechanically connected to the expandable member and the other of which may be mechanically connected to the retainer, as described below with respect to FIGS. 5 and 6. Regardless of a manner in which an expandable member is configured to be expanded or a number of ends of an expandable member that are mechanically connected to an elongated body of an catheter, the expandable members described herein may provide a flow barrier to reduce or prevent antegrade blood flow within a vessel, reduce or prevent retrograde flow of a fluid, and/or may act as a navigation structure that helps a user navigate the catheter through vasculature.

Figure 5:
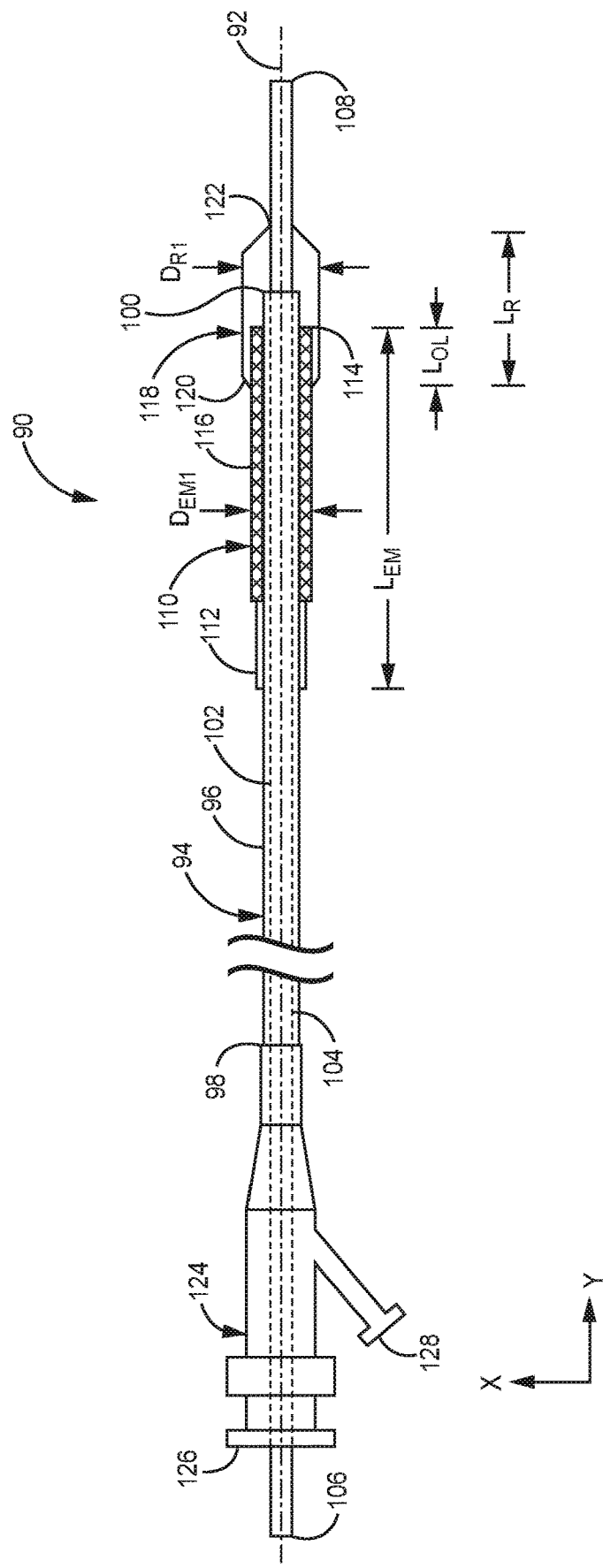
FIG. 5 is a schematic cross-sectional view of another example catheter including an elongated body including an inner member and an outer member, and an expandable member mechanically connected to the outer member and held in a collapsed configuration by a retainer mechanically connected to the inner member, where the cross-section is taken along a longitudinal axis of the catheter.
Figure 6:
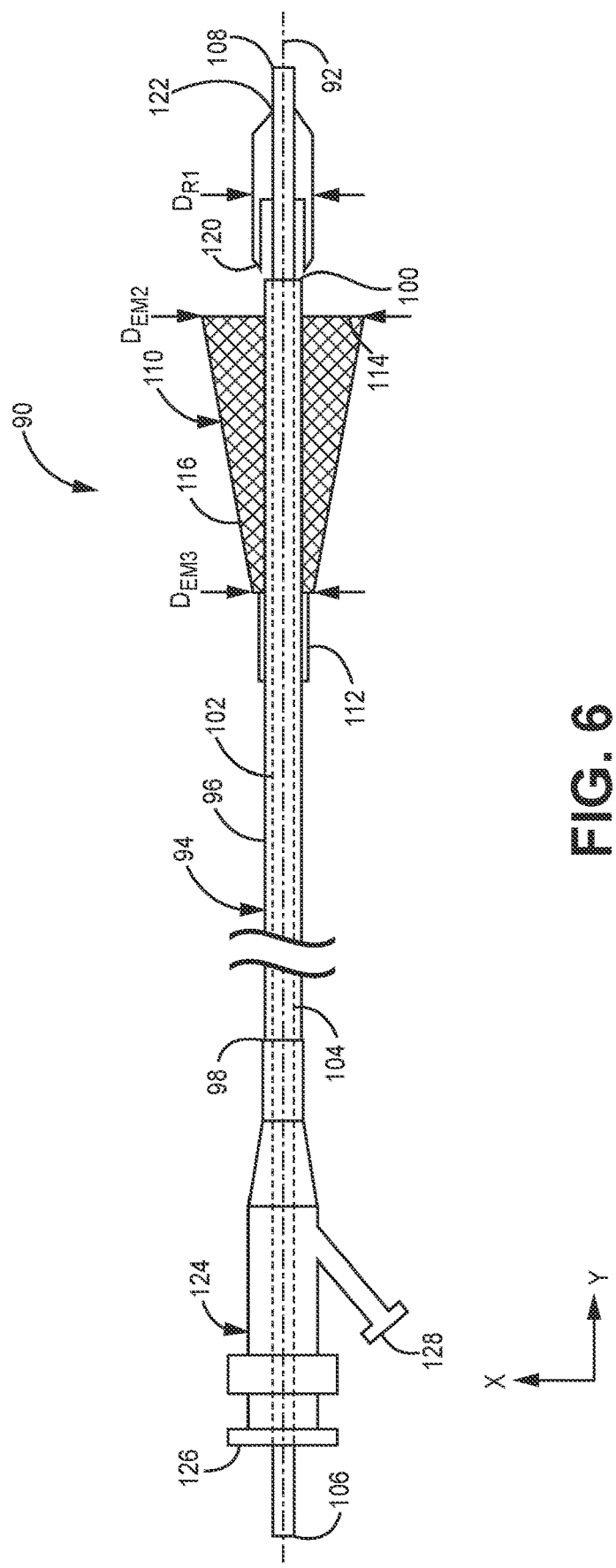
FIG. 6 is a schematic cross-sectional view of the catheter of FIG. 5 with the expandable member in an expanded configuration and released from the retainer, where the cross-section is taken along the longitudinal axis of the catheter.

FIGS. 5 and 6 illustrate another example catheter 90 that includes an expandable member 110 configured to provide a flow barrier to reduce or prevent antegrade blood flow within a vessel, reduce or prevent retrograde flow of a fluid, and/or may act as a navigation structure that helps a user navigate the catheter through vasculature. FIGS. 5 and 6 are schematic cross-sectional views of catheter 90, where the cross-section is taken along a longitudinal axis 92 of catheter 90. Longitudinal axis 92 may be a central longitudinal axis of one or more components of catheter 90, such as an elongated body 94 of catheter 90.

Elongated body 94 of catheter 90 includes an outer member 96, which extends from a proximal end 98 to a distal end 100 and defines a lumen 102. Elongated body 94 further includes an inner member 104 extending from a proximal end 106 to a distal end 108 and at least partially received within lumen 102 defined by outer member 96. Inner member 104 may be slidably received within outer member lumen 102 such that inner member 104 is longitudinally movable relative to outer member 96. As shown in FIG. 5, proximal end 106 of inner member 104 may extend proximally of proximal end 98 of outer member 96. Inner member 104 is configured to be grasped by a clinician at or near proximal end 106 (e.g., either directly or indirectly via a handle, hub, or the like) to move inner member 104 longitudinally relative to outer member 96.

In some examples, outer member 96 and inner member 104 may be threadably connected such that inner member 104 and outer member 96 may be rotated relative to one another in order to move outer member 96 and inner member 104 longitudinally relative to each other. In some examples, inner member 104 and outer member 96 may be threadably connected via a threaded connection provided by external handles respectively coupled to outer member 96 and inner member 104, or via an internal threaded connection. In this manner, longitudinal movement of inner member 104 relative to outer member 96 may be controlled via rotation of inner member 104 relative to outer member 96. Control of longitudinal movement of inner member 104 relative to outer member 96 via relative rotation of inner member 104 and outer member 96 may enable the longitudinal positions of inner member 104 and outer member 96 to be more tightly controlled relative to examples in which an inner member and an outer member are configured to longitudinally slide freely relative to each other. Additionally, or alternatively, a threaded connection between inner member 104 and outer member 96 may keep inner member 104 and outer member 96 longitudinally fixed relative to one another when not being rotated. Although the foregoing example is described with respect to movement of inner member 104 relative to outer member 96, longitudinal movement of outer member 96 relative to inner member 104 may be controlled in a substantially similar manner.

Expandable member 110 extends from a first (e.g., proximal) end 112 to a second (e.g., distal) end 114. In the example of FIGS. 5 and 6, first end 112 of expandable member 110 is mechanically coupled to outer member 96 of elongated body 94 either directly or indirectly (e.g., with a sleeve or another material positioned between second end 114 and outer member 96). For example, first end 112 of expandable member 110 may be bonded, crimped, swaged, welded, or otherwise secured to outer member 96. Expandable member 110 may be similar to expandable member 22 and may include a plurality of struts 116 or an expandable mesh material. As illustrated in FIG. 6, expandable member 110 is configured to be expanded from a collapsed configuration in which expandable member 110 defines diameter $D_{EM1}$ to an expanded configuration in which expandable member 110 defines a larger diameter. In the expanded configuration, expandable member 110 may engage with a vessel wall of a patient, e.g., expandable member 110 may contact the vessel walls to block fluid flow past expandable member 110 and/or to deflect or otherwise change an orientation of a portion of catheter 90 distal to expandable member 110.

Catheter 90 further includes a retainer 118 extending from a proximal portion 120 to a distal portion 122. As illustrated in FIG. 5, distal portion 122 of retainer 118 is mechanically connected to a portion of inner member 104 that extends distally of distal second end 114 of expandable member 110, such as by bonding, crimping, swaging, welding, or otherwise securing distal portion 122 of retainer 118 to inner member 104. Retainer 118 is configured to overlap second end 114 of expandable member 110 and retain expandable member 110 in the collapsed configuration, as illustrated in FIG. 1. For example, proximal portion 120 of retainer 118 is configured to overlap a distal portion of expandable member 110 that includes second end 114 of expandable member 110. Proximal portion 120 may have an overlap length "$L_{oL}$" that defines the portion of expandable retainer 118 that overlaps expandable member 110.

In some examples, catheter 90 further may include a hub 124 positioned at proximal end 98 of outer member 96. Hub 124 may include at least one of a first port 126 or a second port 128, one or both of which may provide access to lumen 102 defined by outer member 96 and/or a lumen defined by inner member 104 in examples in which inner member 104 defines a lumen (e.g., through which a substance may be delivered to, or aspirated from, a vessel of a patient).

FIG. 6 is a schematic cross-sectional view of catheter 90 of FIG. 5 with expandable member 110 in the expanded configuration and released from retainer 118, where the cross-section is taken along longitudinal axis 92 of catheter 90. FIG. 6 illustrates catheter 90 after inner member 104 has been moved distally, relative to outer member 96, until proximal portion 120 of retainer 118 no longer overlaps second end 114 of expandable member 110, thereby releasing second end 114 of expandable member 110. After retainer 118 releases second end 114 of expandable member 110, expandable member 110 can expand (e.g., self-expand) radially outward from the collapsed configuration illustrated in FIG. 5 to the expanded configuration illustrated in FIG. 6 while first end 112 remains mechanically coupled to elongated body 94.

One or more features of catheter 90 of FIGS. 5 and 6 may be substantially similar to the corresponding features of catheter 10 described above with respect to FIGS. 1 and 2 (or catheter 50 of FIGS. 3 and 4) and will not be discussed again in detail here. For example, expandable member 110 and hub 124 may be substantially similar to expandable member 22 and hub 44 of catheter 10, respectively. Retainer 118 may be similar to expandable retainer 32 of catheter 10 in one or more aspects. For example, retainer 118 may be formed from one or more biocompatible materials from which expandable retainer 32 may be formed, such as nylon, polyethylene terephthalate (PET), polyethylene (such as crosslinked polyethylene), polyurethane, polyvinyl chloride, silicone elastomer, or the like. Proximal portion 120 of retainer 118 may comprise two or more tabs defining spaces therebetween, as described above with respect to proximal portion 34 of expandable retainer 32.

In some examples, the configuration of retainer 118 when proximal portion 120 of retainer 118 overlaps second end 114 of expandable member 110 and retains expandable member 110 in the collapsed configuration may be substantially similar to the configuration of expandable retainer 32 when expandable retainer 32 is in the collapsed configuration. For example, a retainer diameter $D_{R1}$ of retainer 118 and/or a retainer length $L_R$ of retainer 118 may be substantially similar to collapsed retainer diameter $D_{EM1}$ and/or retainer length $L_R$ of expandable retainer 32, respectively. As with catheter 10, a ratio of overlap length $L_{oL}$ of proximal portion 120 of retainer 118 to length $L_{EM}$ of expandable member 110 may be about 1:2, 1:3, 1:4 or 1:5, although the extent to which proximal portion 120 of retainer 118 overlaps expandable member 110 may vary in other examples.

Catheter 90 generally differs from catheter 10 in the configuration of the features of catheter 90 that enable proximal portion 120 of retainer 118 to release second end 114 of expandable member 110. For example, elongated body 94 includes outer member 96, to which expandable member 110 is mechanically connected, and inner member 104, to which retainer 118 is mechanically connected, instead of elongated body 14 that may comprise a single member to which both expandable member 22 and expandable retainer 32 are attached. As discussed above, inner member 104 is received within lumen 102 defined by outer member 96 such that inner member 104 and outer member 96 are longitudinally movable relative to one another. Catheter 90 further may differ from catheter 10 in that proximal portion 120 of retainer 118 is configured to release second end 114 of expandable member 110 when inner member 104 and retainer 118 are moved away from expandable member 110 (e.g., distally) until proximal portion 120 of retainer 118 no longer overlaps second end 114, instead of releasing second end 26 of expandable member 22 by expanding expandable retainer 32 with an inflation fluid delivered via lumen 38 and openings 42A, 42B.

In some other examples, first end 112 of expandable member 110 may be distal to second end 114 of expandable member 110 instead being proximal to second end 114. In such other examples, first end 112 of expandable member 110 may be mechanically connected to inner member 104 and distal portion 122 of retainer 118 may be mechanically connected to outer member 96 such that distal portion 122 of retainer 118 is configured to overlap second end 114 of expandable member 110. Thus, in such other examples, a funnel shape defined by expandable member 110 when expandable member 110 is in the expanded configuration may have a mouth facing a proximal direction (e.g., toward hub 124) instead of a distal direction. In such examples, distal portion 122 of retainer 118 is configured to release second end 114 of expandable member 110 when inner member 104 and expandable member 110 are moved relative to retainer 118 until distal portion 122 no longer overlaps second end 114 of expandable member 110. In other examples, distal portion 122 of retainer 118 may be configured to release second end 114 of expandable member 110 when outer member 96 and retainer 118 are moved relative to expandable member 110 until distal portion 122 no longer overlaps second end 114 of expandable member 110. Thus, second end 114 of expandable member 110 generally may be released from retainer 118 via relative movement (e.g., longitudinal and/or rotational) of inner member 104 and outer member 96.

Retainer 118 further may differ from expandable retainer 32 in that retainer 118 may not necessarily be expandable. For example, a composition of a material from which retainer 118 is formed may differ from a material from which retainer 32 is formed. Values of one more mechanical, physical, or chemical properties of the material from which retainer 118 is formed may thus differ from the corresponding values of one or more properties of the material from which expandable retainer 32 is formed. For example, a value of an elastic modulus of retainer 118 may be less than a value of the elastic modulus of expandable retainer 32, as expandable retainer 32 is configured to release second end 26 of expandable member 22 by expanding from collapsed retainer diameter $D_{R1}$ to expanded retainer diameter $D_{R2}$.

Figure 7A:
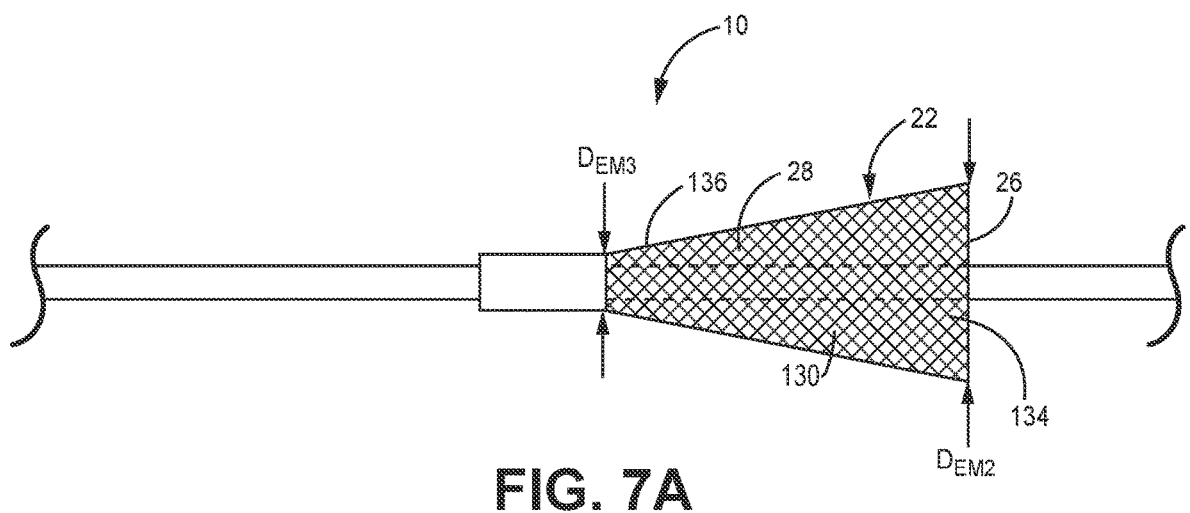
FIG. 7A is a perspective view of the elongated body and the expandable member of the catheter of FIG. 1, and a layer of occlusive material attached to the expandable member.
Figure 7B:
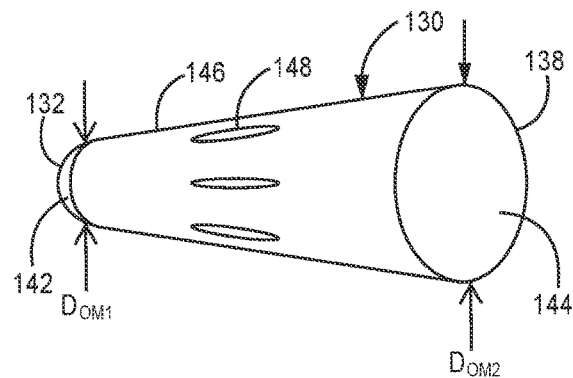
FIG. 7B is a perspective view of the layer of occlusive material of the catheter of FIG. 1.

FIGS. 7A and 7B illustrate expandable member 22 of catheter 10 of FIG. 1 and an occlusive material 130 that catheter 10 optionally may include in some examples. FIG. 7A is a perspective view of elongated body 14, expandable member 22, and occlusive material 130, and illustrates an example configuration of the attachment of occlusive material 130 to expandable member 22. FIG. 7B is a perspective view of occlusive material 130 in an unfolded or expanded configuration. Occlusive material 130 is illustrated in FIGS. 7A and 7B and described with respect thereto as being a structure of catheter 10 of FIGS. 1 and 2. However, any of the other example catheters described herein (e.g., catheter 50 or catheter 90) may include occlusive material 130, which may be attached to expandable member 62 or expandable member 110 in a manner substantially similar to that described below with respect to catheter 10.

Occlusive material 130 may be attached to expandable member 22 and configured to expand with the expandable member 22 from the collapsed configuration to the expanded configuration. In other examples, occlusive material 130 may not necessarily be expandable, but instead may be folded into the collapsed configuration and configured to unfold into an unfolded configuration that approximates the expanded configuration of expandable member 22. Occlusive material 130 is primarily described herein as being "expandable" from the collapsed configuration to the expanded configuration; however, it should be understood that occlusive material 130 may not necessarily be expandable in some such examples, but instead may be configured to unfold from the collapsed configuration when expandable member 22 is expanded.

Occlusive material 130 may be a flexible, substantially fluid-impermeable and/or hydrophobic material such as a polymer (e.g., ePTFE), which in some examples may be the same material from which expandable member 22 is formed. Occlusive material may be substantially fluid-impermeable such that occlusive material 130 does not permit a physiologically significant flow of blood therethrough. For example, occlusive material 130 may block 90-99% of a flow of fluid through a vessel or may block any other portion of the flow of fluid through the vessel such that any remaining fluid flow not blocked by occlusive material 130 is not physiologically significant. Expandable member 22 and occlusive material 130 together may help prevent retrograde flow of a substance introduced into a vessel during a medical procedure (e.g., an embolic substance) past expandable member 22 and/or may provide a temporary vessel-occlusion device by reducing or preventing antegrade blood flow within the vessel, e.g., distal of expandable member 22.

As illustrated in FIG. 7A, occlusive material 130 may be attached to expandable member 22 using any suitable technique. Expandable member 22 may define an inner surface 134 and an outer surface 136 that is radially outwards of inner surface 134. In some examples, a proximal portion 132 (illustrated in FIG. 7B) of occlusive material 130 may be attached to inner surface 134 near first end 24 of expandable member 22 (e.g., at or near an apex of expandable member 22 when expandable member 22 is in the expanded configuration). Inner surface 134 may include inner surfaces of plurality of struts 28 in examples in which expandable member includes plurality of struts 28 or an inner surface of an expandable mesh material of expandable member 22.

In some examples, occlusive material 130 may be attached to inner surface 134 via an adhesive positioned between occlusive material 130 and inner surface 134. Additionally, or alternatively, proximal portion 132 of occlusive material 130 may be positioned between first end 24 of expandable member 22 and elongated body 14 such that proximal portion 132 of occlusive material 130 is attached to first end 24 of expandable member 22 when first end 24 of expandable member 22 is bonded, crimped, swaged, welded, or otherwise attached to elongated body 14.

In examples in which occlusive material 130 is attached to inner surface 134 and a mouth of a funnel defined by expandable member 22 faces distally, occlusive material 130 also may be attached to inner surface 134 at distal portion 138 and/or at one or more other points on occlusive material 130. Attaching occlusive material 130 to expandable member 22 at both proximal portion 132 and distal portion 138 in such examples may help prevent occlusive material 130 from collapsing radially inward toward central longitudinal axis 12 when expandable member 22 and occlusive material 130 are expanded within a vessel of a patient and antegrade blood flow exerts force on occlusive material 130. To help retain occlusive material 130 against expandable member 22 in such examples, occlusive material 130 may be formed from or otherwise include a stiff, thin material (e.g., a biaxially oriented nylon or polyester or other similar materials), which may bias occlusive material 130 to self-expand against inner surface 134. Additionally, or alternatively, occlusive material 130 may include one or more rigid ribs, which may bias occlusive material 130 to self-expand against inner surface 134.

In some other examples, a proximal portion 132 (illustrated in FIG. 7B) of occlusive material 130 may be attached to outer surface 136 defined by expandable member 22. For example, proximal portion 132 of occlusive material 130 may be attached to outer surface 136 near first end 24 of expandable member 22 (e.g., at or near an apex of expandable member 22 when expandable member is in the expanded configuration). Outer surface 136 may include outer surfaces of plurality of struts 28, in examples in which expandable member includes plurality of struts 28, or an outer surface of an expandable mesh material of expandable member 22. In some examples, occlusive material 130 may be attached to outer surface 136 via an adhesive positioned between occlusive material 130 and outer surface 136. Occlusive material 130 also may be attached to outer surface 136 at distal portion 138 and/or at one or more other points on occlusive material 130. In any examples in which occlusive material 130 is attached to outer surface 136 and expandable member 22 and a mouth of a funnel defined by expandable member 22 faces distally, antegrade blood flow may be reduced or occluded as antegrade flow pushes occlusive material 130 against expandable member 22 when expandable member 22 and occlusive material 130 are in the expanded configurations. That is, antegrade blood flow may cause occlusive material 130 to seal against expandable member 22, thereby reducing or occluding blood flow.

In any examples in which expandable member 22 and occlusive material 130 define a funnel having a distal-facing mouth, the orientation of expandable member 22 and occlusive material 130 may reduce or prevent antegrade-flowing blood from pooling within the funnel. Additionally, or alternatively, a distal-facing mouth of a funnel defined by expandable member 22 when expandable member 22 is in the expanded configuration may enable expandable member 22 to reduce retrograde flow of a substance (e.g., an embolic substance) into a parent vessel from a target vessel in which expandable member 22 is deployed by capturing retrograde-flowing substances within the funnel. Expandable member 22 and occlusive material 130 later may be withdrawn from the vessel and removed from the patient. For example, expandable member 22 may be withdrawn into an outer sheath (not shown), which then may be removed from the patient. In some examples, expandable member 22 may remain in the expanded configuration until expandable member 22 is drawn into an outer sheath, although in other examples expandable member 22 may be collapsed toward or into the collapsed configuration prior to withdrawal of expandable member 22 into an outer sheath.

As illustrated in FIG. 7B, proximal portion 132 of occlusive material 130 may define a proximal opening 142 and a distal portion 138 of occlusive material 130 may define distal opening 144. Proximal opening 142 may be sized to receive elongated body 14 during a method of manufacturing catheter 10. For example, proximal portion 132 defining proximal opening 142 may have an expanded diameter "$D_{EM1}$," which in some examples may be substantially similar to diameter $D_{EM3}$ (shown in FIG. 2) of first end 24 of expandable member 22 when expandable member 22 is in the expanded configuration. Distal portion 138 defining distal opening 144 may have an expanded diameter $D_{EM2}$, which in some examples may be substantially similar to expanded diameter $D_{EM2}$(shown $D_{EM2}$ (shown in FIG. 2) of second end 26 of expandable member 22 when expandable member 22 is in the expanded configuration.

In examples in which occlusive material 130 is attached to outer surface 136 defined by expandable member 22, a material from which occlusive material 130 is formed may be stretchable enough to be stretched over expandable member 22 when expandable member 22 is in the expanded configuration. Additionally, or alternatively, dimensions of occlusive material 130 may be slightly larger than corresponding dimensions of expandable member 22. For example, dimensions of occlusive material 130 (e.g., $D_{OM1}$ or $D_{OM2}$) may be sufficiently larger than respective ones of diameter $D_{EM3}$ and $D_{EM2}$ of expandable member 22 to receive expandable member 22 while allowing occlusive material 130 to seal against expandable member 22 under the force of antegrade blood flow.

Occlusive material 130 further may define an outer surface 146, which may define at least one opening 148. In the illustrated example of FIG. 7B, outer surface 146 defines at least three openings 148. Openings 148 may be configured to reduce air pockets that may occur in expandable member 22 when expandable member 22 is in the expanded configuration and positioned within blood flow within a vessel of a patient. In examples in which occlusive material 130 defines at least one opening 148, occlusive material 130 nonetheless substantially blocks fluid flow therethrough (e.g., does not permit a physiologically significant flow of blood therethrough, as described above). Thus, even in examples in which occlusive material 130 defines at least one opening 148, occlusive material 130 may be used to reduce or occlude blood flow within a vessel instead of as a filter configured to permit a greater (e.g., physiologically significant) flow of blood therethrough.

Figure 8:
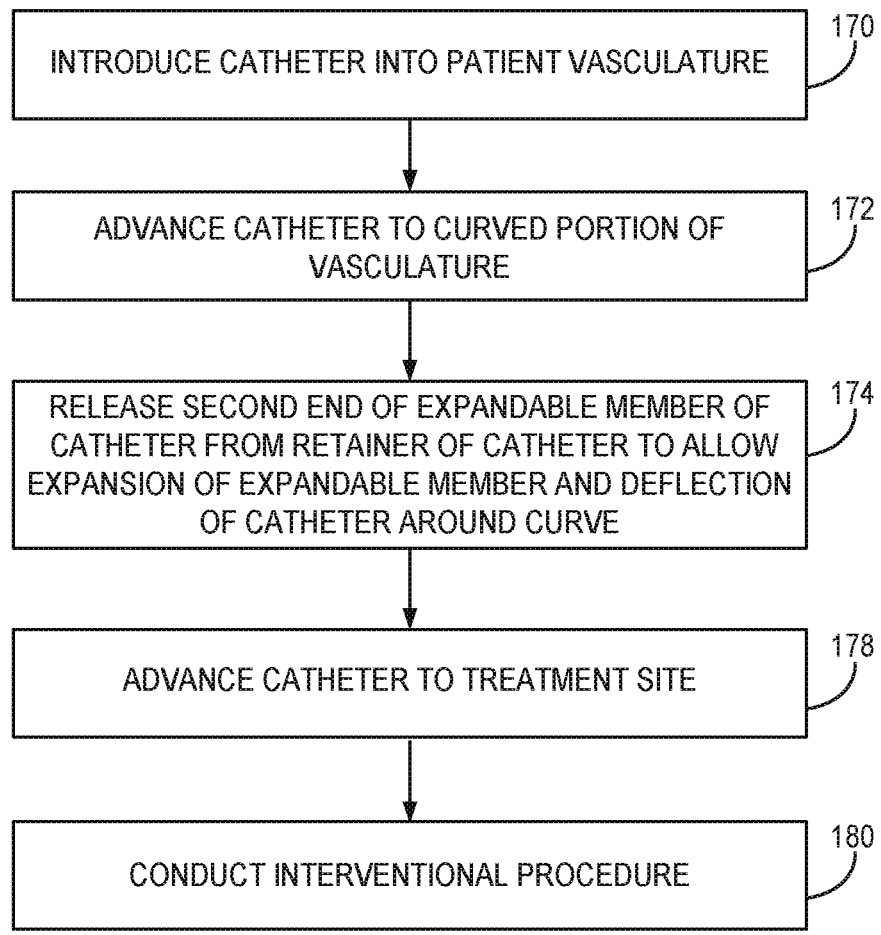
FIG. 8 is a flow diagram illustrating an example method of deploying and using a catheter as described herein.

FIG. 8 is a flow diagram illustrating an example method of deploying and using a catheter, such as catheter 10, within the vasculature of a patient as described herein. The method of FIG. 8 is described in conjunction with FIGS. 9A and 9B. FIGS. 9A and 9B illustrate a series of side views showing catheter 10 of FIGS. 1 and 2 being operated in accordance with the technique described with respect to FIG. 8. For example, FIGS. 9A and 9B illustrate catheter 10 being advanced within a vessel 150, which defines a lumen 152, to a curved portion 154 of vessel 150, as well as expandable member 22 being expanded into contact with an inner surface 156 defined by vessel 150 to deflect a portion of elongated body 14 distal to expandable member 22 about a deflection point 158. While FIGS. 8-9B are described in the context of catheter 10 of FIGS. 1 and 2, the technique of FIG. 8 may be used in conjunction with other techniques or other catheters (e.g., catheter 50 of FIGS. 3 and 4 or catheter 90 of FIGS. 5 and 6).

FIG. 9A shows a distal portion 160 of catheter 10 positioned within vessel 150 of the vasculature of a patient. Distal portion 160 of catheter 10 may include at least the portion of elongated body 14 shown in FIG. 9A, expandable member 22, and expandable retainer 32. Prior to positioning catheter 10 as shown in FIG. 9A, a clinician may create an insertion path from an entry point accessible from outside a patient to a target site into the vasculature, e.g., with the aid of a needle or another device having a cutting surface. The clinician may introduce a guidewire into the insertion path, e.g., through the needle or another device. Once the insertion path has been created, the clinician may introduce distal portion 160 of catheter 10 into the insertion path over the guidewire, with expandable member 22 and expandable retainer in the respective collapsed configurations. In these examples, catheter 10 may function as a guide catheter, through which another catheter may be inserted, or may function as both a guide catheter and an aspiration catheter or other catheter. In some cases, the navigability of catheter 10 provided by expandable member 22 may permit catheter 10 to be navigated to a target treatment site in vasculature of a patient without the aid of a guide catheter. In other examples, a guide catheter or another guide device may be introduced over the guidewire and then catheter 10 may be inserted through a lumen of the guide device, rather than directly over the guidewire without the aid of a guide device. Hub 44 of catheter 10 (shown in FIGS. 1 and 2) may remain outside of the body of the patient.

In the example method of FIG. 8, at least distal portion 160 of catheter 10 may be introduced into vessel 150 (170). In some examples, vessel 150 may be a feeding vessel that feeds a target vessel in which an interventional procedure may be performed, such as a procedure to deliver an embolic substance to treat an AVM, a procedure to treat ischemic stroke, or other vascular intervention procedure. After introduction of distal portion 160 of catheter 10 into the vasculature of the patient, the clinician then may advance distal portion 160 through vessel 150 until one or more portions of distal portion 160 (e.g., distal end 18 of elongated body 14, expandable member 22, and expandable retainer 32) reach curved portion 154 of vessel 150 (172).

Depending on one or more factors, such as a stiffness of one or more of elongated body 14, expandable member 22, expandable retainer 32, or an angle formed by curved portion 154 of vessel 150, distal portion 160 of catheter 10 may experience a resistive force applied by inner surface 156 of vessel 150 as distal portion 160 is advanced into curved portion 154 when distal portion 160 is in the substantially linear configuration illustrated in FIG. 9A. In some examples, the resistive force applied by inner surface 156 of vessel 150 may make it more difficult for the clinician to advance distal portion 160 through the portion of lumen 152 defined by curved portion 154 of vessel 150 without applying excessive distal pushing force to distal portion 160.

In order to help advance distal portion 160 through the portion of lumen 152 defined by curved portion 154 of vessel 150 without applying excessive pushing force to distal portion 160, the clinician may deploy expandable member 22 to cause a portion of elongated body 14 distal to first end 24 of expandable member 22 to deflect by bending elongated body 14 about deflection point 158, which is proximal to first end 24 of expandable member 22. For example, clinician may release second end 26 of expandable member 22 from expandable retainer 32 to allow self-expansion or balloon-aided expansion of expandable member 22 from the collapsed configuration shown in FIG. 9A to the expanded configuration shown in FIG. 9B and deflection of a portion of catheter 10 distal to deflection point 158 around the curved shape of curved portion 154 of vessel 150 (174). That is, a radial force applied by expandable member 22 to inner surface 156 of vessel 150 when expandable member 22 is in the expanded configuration may be sufficient to cause deflection of the portion of catheter 10 distal to deflection point 158. However, the radial force applied by expandable member 22 to inner surface 156 may not necessarily be sufficient to fix catheter 10 in place within vessel 150.

In the example of catheter 10, the clinician may release second end 26 of expandable member 22 from expandable retainer 32 by introducing a fluid into expandable retainer 32 to expand expandable retainer 32. For example, the clinician may introduce the fluid into lumen 38 defined by elongated body 14 via first port 46 and/or second port 48 of hub 44. The fluid introduced into lumen 38 may exit lumen 38, via openings 42A, 42B defined by outer wall 40 defined by elongated body 14. As illustrated in FIG. 9B, expandable retainer 32 further may define an inner surface 176. Force exerted by the fluid on inner surface 176 of expandable retainer 32 may cause expandable retainer 32 to expand to the expanded configuration, thereby releasing second end 26 of expandable member 22 while first end 24 remains mechanically coupled to elongated body 14. In examples in which expandable member 22 is self-expanding, expandable member 22 may expand radially outward in response to its second end 26 being released from expandable retainer 32.

In examples in which the technique of FIG. 8 is used in conjunction with catheter 90 of FIGS. 5 and 6, the clinician instead may release second end 114 of expandable member 110 from retainer 118 by moving inner member 104 relative to outer member 96, either by moving inner member 104, outer member 96, or both inner and outer members 104, 96, thereby distally moving retainer 118 and causing retainer 118 to release second end 114 of expandable member 110. In examples in which expandable member 22 is self-expanding, after retainer 118 releases second end 114 of expandable member 110, expandable member 110 expands radially outward from the collapsed configuration illustrated in FIG. 5 to the expanded configuration illustrated in FIG. 6 while first end 112 remains mechanically coupled to elongated body 94.

As expandable member 22 expands from the collapsed configuration shown in FIG. 9A to the expanded configuration shown in FIG. 9B, a portion of expandable member 22 contacts inner surface 156 defined by vessel 150 and helps to better conform elongated body 14 to the curved shape of curved portion 154. In some examples, expandable member 22 may be self-expandable. In other examples, expandable member 22 may be expandable via actuation of a push/pull wire attached to expandable member 22 (not shown), or any other suitable feature configured to expand and/or collapse expandable member 22. In examples in which expandable member 22 defines a funnel, such as the example illustrated in FIG. 9A, at least second end 26 of expandable member 22 may contact inner surface 156. In any such examples, resistive force applied by inner surface 156 to expandable member 22 when expandable member 22 is in substantial conformation with inner surface 156 may be translated to elongated body 14 via expandable member 22, causing deflection of a portion of elongated body 14 distal to expandable member 22 about deflection point 158.

With the portion of elongated body 14 distal to expandable member 22 deflected about deflection point 158, distal end 18 of elongated body 14 may be re-oriented away from inner surface 156 such longitudinal axis defined by catheter 10 and elongated body 14 (e.g., longitudinal axis 12, shown in FIG. 1) is substantially parallel to a longitudinal axis defined by vessel 150 (not shown). Re-orienting distal end 18 of elongated body 14 in this manner may alleviate resistance applied to distal end 18 by inner surface 156, thereby reducing the amount of distal pushing force needed to continue advancing distal portion 160 of catheter 10. Additionally, or alternatively, the clinician may deploy expandable member 22 to steer distal end 18 of elongated body into a desired one of multiple vessels that branch off from vessel 150. In this manner, expandable member 22 may enable steering of distal portion 160 of catheter 10 through tortuous regions of the vasculature of the patient along a desired path of travel to a treatment site within a target vessel, which may help increase the efficiency and/or improve a clinical outcome of the procedure.

The clinician then may continue to advance distal portion 160 of catheter 10 through vessel 150 to a treatment site within a target vessel, which may be vessel 150 or another vessel within the vasculature of the patient (178). In some examples, expandable member 22 may be collapsed back toward, or into, the collapsed configuration before the clinician continues to advance distal portion 160. For example, as previously mentioned, catheter 10 may include a push/pull wire attached to expandable member 22 (not shown) that may be actuated to expand and/or collapse expandable member 22, or any other suitable feature that may be configured to expand and/or collapse expandable member 22. Additionally, or alternatively, expandable retainer 32 may be collapsed back toward, or into, the collapsed configuration before the clinician continues to advance distal portion 160 through vessel 150 toward the treatment site, such as by aspirating fluid used to expand expandable retainer 32 from expandable retainer 32.

In some other examples, catheter 10 may be a guide catheter defining a lumen through which an interventional catheter (e.g., a catheter configured for aspiration and/or delivery of an interventional device such as a thrombectomy device or stent retriever, and/or a drug or medical agent) may be delivered. In such examples, instead of advancing distal portion 160 of catheter 10 through vessel 150 to the treatment site, the clinician instead may leave distal portion 160 of catheter 10 in place within vessel 150, as illustrated in FIG. 9B, and introduce the interventional catheter through catheter 10 to the treatment site.

In examples in which the clinician has advanced distal portion 160 to the treatment site with expandable member 22 in the collapsed configuration, the clinician may expand expandable member 22 prior to conducting the interventional procedure. With expandable member 22 in the expanded configuration at the treatment site, expandable member 22 may be in contact with inner surface 156 of vessel 150, thereby reducing or occluding blood flow within vessel 150. For example, radial force applied by expandable member 22 to inner surface 156 of vessel 150 when expandable member 22 is in the expanded configuration may be sufficient to reduce or occlude blood flow within vessel 150. However, the radial force applied by expandable member 22 to inner surface 156 when expandable member 22 is at the treatment site may not necessarily be sufficient to fix catheter 10 in place within vessel 150. With distal portion 160 of catheter 10 positioned at the treatment site within the target vessel, the clinician then may conduct an interventional procedure, such as a procedure to introduce an embolic substance for treatment of an AVM, ischemic stroke, or other condition via thrombectomy, embolectomy, aspiration, aneurysm treatment procedure, stent placement, or any other suitable procedure (180). The clinician then may withdraw distal portion 160 of catheter 10 from vessel 150 and remove distal portion 160 from the patient (e.g., following the interventional procedure). For example, the clinician may withdraw distal portion 160 into an outer sheath or another catheter (not shown), which then may be removed from the patient. In some examples, expandable member 22 may remain in the expanded configuration until expandable member is drawn into the outer sheath or other catheter. In other examples, the clinician may collapse expandable member 22 toward or into the collapsed configuration prior to withdrawing expandable member 22 (e.g., by actuating a push/pull wire attached to expandable member 22) into the outer sheath or other catheter.

Figure 10:
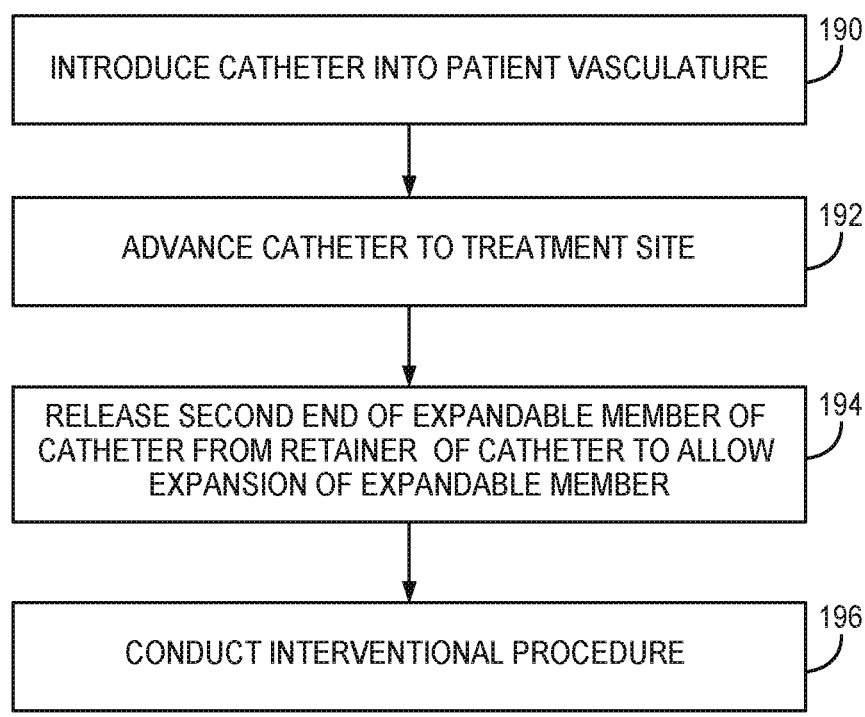
FIG. 10 is a flow diagram illustrating another example method of using a catheter as described herein.

FIG. 10 is a flow diagram illustrating another example method of deploying and using a catheter, such as catheter 10, within the vasculature of a patient as described herein. While FIG. 10 is described in the context of catheter 10 of FIGS. 1 and 2, the techniques of FIG. 10 may be used in conjunction with other techniques or other catheters (e.g., catheter 50 of FIGS. 3 and 4 or catheter 90 of FIGS. 5 and 6). As with the flow diagram of FIG. 8, the flow diagram of FIG. 10 is described in conjunction with FIGS. 9A and 9B. While FIG. 10 is described with reference to catheter 10 of FIGS. 1 and 2, the technique of FIG. 10 may be used in conjunction with other techniques or other catheters (e.g., catheter 50 of FIGS. 3 and 4 or catheter 90 of FIGS. 5 and 6).

One or more steps of the example method of FIG. 10 may be substantially similar to the corresponding steps of example method of FIG. 8 and will not be discussed again in detail here. For example, in the method of FIG. 10, a clinician may introduce at least distal portion 160 of catheter 10 introduced into vessel 150 (190) in a manner substantially as described with respect to (170) of FIG. 8. The clinician may advance distal portion 160 of catheter 10 through vessel 150 to a treatment site within a target vessel, which may be vessel 150 or another vessel within the vasculature of the patient (192), in a manner substantially as described with respect to (178) of FIG. 8. For example, the clinician may release second end 26 of expandable member 22 from expandable retainer 32 by introducing a fluid into expandable retainer 32 to expand expandable retainer 32, or, in the example of catheter 90, by moving inner member 104 and retainer 118 distally until proximal portion 120 of retainer 118 no longer overlaps second end 114 of expandable member 110 (194) in a manner substantially as described with respect to (174) of FIG. 8 and such that expandable member engages with a vessel wall at or near the treatment site. With distal portion 160 of catheter 10 positioned at the treatment site within the target vessel, the clinician then may conduct an interventional procedure, such as a procedure to introduce an embolic substance for treatment of an AVM, ischemic stroke, or other condition via embolectomy, aneurysm treatment procedure, stent placement, or any other suitable procedure (196) in a manner substantially as described with respect to (180) of FIG. 8.

The example method of FIG. 10 may differ from the example of FIG. 8 in that the clinician may release second end 26 of expandable member 22 from expandable retainer 32 to expand expandable retainer 32 (194) after advancing distal portion 160 of catheter 10 to the treatment site (192) instead of before distal portion 160 of catheter 10 reaches the treatment site. For example, if a vessel through which distal portion 160 of catheter 10 is advanced is substantially linear between the entry point and the treatment site, the clinician may not necessarily deploy expandable member 22 to help steer distal portion 160 of catheter 10. Thus, in such examples, the clinician may expand expandable retainer 32 to release second end 26 of expandable member 22 from expandable retainer 32 when distal portion 160 of catheter 10 is at the treatment site.

The example methods of FIGS. 8 and 10 are intended to be exemplary in nature. Thus, the example methods of FIGS. 8 and 10 are not limited to the steps described above and are not intended to be mutually exclusive. For example, an example method of deploying and using a catheter (e.g., catheter 10) within the vasculature of a patient may include releasing second end 26 of expandable member 22 from expandable retainer 32 to allow expansion of expandable member 22 and deflection of a portion of catheter 10 distal to deflection point 158 around a curved shape of curved portion 154 of vessel 150 (174) and collapsing expandable member 22 back toward or into the collapsed configuration after the clinician has advanced distal portion 160 of catheter 10 past curved portion of vessel 150. In such examples, expandable member 22 may be in a substantially collapsed configuration when the clinician advances distal portion 160 of catheter 10 to the treatment site but no longer retained at second end 26 by expandable retainer 32. In such examples, the clinician may re-expand expandable member 22 at the treatment site (e.g., by actuating a push/pull wire attached to expandable member 22) without necessarily expanding expandable retainer 32.

Various examples have been described. These and other examples are within the scope of the following claims.

What is claimed is:

1. A catheter comprising:
   an elongated body;
   an expandable member extending from a first end to a second end, the first end of the expandable member being mechanically connected to the elongated body, wherein the expandable member is configured to expand radially outward away from the elongated body from a collapsed configuration to an expanded configuration; and
   a retainer comprising a first portion and a second portion, wherein the first portion is mechanically connected to the elongated body or to an inner member disposed within a lumen of the elongated body, wherein the second portion is configured to overlap the second end of the expandable member to hold the expandable member in the collapsed configuration, and wherein the retainer is configured to move relative to the expandable member to release the second end of the expandable member and enable the expandable member to expand into the expanded configuration.

2. The catheter of claim 1, wherein the first end of the expandable member is a proximal end and the second end of the expandable member is a distal end.

3. The catheter of claim 1, wherein the first end of the expandable member is a distal end and the second end of the expandable member is a proximal end.

4. The catheter of claim 1, wherein the second portion of the retainer comprises a proximal portion and wherein the first portion of the retainer comprises a distal portion, wherein the distal portion of the retainer is mechanically connected to the elongated body distal to the expandable member, and wherein the proximal portion of the retainer is configured to overlap a distal portion of the expandable member and hold the expandable member in the collapsed configuration.

5. The catheter of claim 1, wherein the retainer is expandable to release the second end of the expandable member to enable the expandable member to expand from the collapsed configuration to the expanded configuration.

6. The catheter of claim 5, wherein the retainer comprises a balloon.

7. The catheter of claim 6, wherein the elongated body defines the lumen and an outer wall defining at least one opening that fluidically connects the lumen and the balloon wherein the retainer is configured to expand when a fluid is introduced into the balloon via the lumen.

8. The catheter of claim 1, wherein the elongated body comprises the inner member and an outer member, and wherein the expandable member is mechanically connected to the outer member and the retainer is mechanically connected to the inner member, wherein longitudinal movement of the inner member relative to the outer member moves the retainer relative to the expandable member to release the second end of the expandable member from the retainer, and wherein the expandable member is configured to expand from the collapsed configuration to the expanded configuration when the second end of the expandable member is released from the retainer.

9. The catheter of claim 1, wherein the expandable member is configured to engage with a vessel wall of a patient when the expandable member is in the expanded configuration.

10. The catheter of claim 9, wherein when the vessel wall defines a curved shape and when the expandable member is engaged with the vessel wall, the expandable member is configured to deflect a portion of the elongated body distal to the expandable member.

11. The catheter of claim 1, wherein the expandable member defines a funnel in the expanded configuration.

12. The catheter of claim 11, wherein a mouth of the funnel faces a distal direction.

13. The catheter of claim 1, further comprising a layer of occlusive material attached to the expandable member, wherein the layer of occlusive material and the expandable member are configured to occlude blood flow within a vessel of a patient when the layer of occlusive material and the expandable member are in the expanded configuration.

14. The catheter of claim 13, wherein the layer of occlusive material comprises a polymer.

15. The catheter of claim 13, wherein the layer of occlusive material defines at least one opening configured to reduce air pockets in the expandable member when the expandable member is in the expanded configuration in blood flow of the patient.

16. The catheter of claim 1, wherein the expandable member comprises a hydrophobic coating.

17. The catheter of claim 1, wherein the expandable member is self-expandable.

18. The catheter of claim 17, wherein the self-expandable member comprises a shape-memory material.

19. A catheter comprising:
an elongated body;
an expandable member extending from a first end to a second end, the first end of the expandable member being mechanically connected to the elongated body and the second end of the expandable member being unconnected to the elongated body, wherein the expandable member is configured to expand radially outward away from the elongated body from a collapsed configuration to an expanded configuration, and wherein the expandable member defines a funnel in the expanded configuration; and
a retainer comprising a first portion and a second portion, wherein the first portion is mechanically connected to the elongated body or to an inner member disposed within a lumen of the elongated body, wherein the second portion is configured to overlap only the second end to hold the expandable member in the collapsed configuration, wherein the retainer is configured to move relative to the expandable member to release the second end of the expandable member to enable the expandable member to expand from the collapsed configuration to the expanded configuration.

20. The catheter of claim 19, wherein the first end of the expandable member is a proximal end and the second end of the expandable member is a distal end.

21. The catheter of claim 19, wherein the first end of the expandable member is a distal end and the second end of the expandable member is a proximal end.

22. The catheter of claim 19, wherein the retainer comprises a balloon.

23. The catheter of claim 22, wherein the elongated body defines the lumen and an outer wall defining at least one opening that fluidically connects the lumen and the retainer, wherein the balloon is configured to expand when a fluid is introduced into the retainer via the lumen.

24. The catheter of claim 19, wherein the elongated body comprises the inner member and an outer member, and wherein the expandable member is mechanically connected to the outer member and the retainer is mechanically connected to the inner member, wherein longitudinal movement of the inner member relative to the outer member moves the retainer longitudinally relative to the expandable member to release the second end of the expandable member from the retainer.

25. The catheter of claim 24, wherein the inner member and the outer member are threadably connected and configured for rotational movement relative to one another, and wherein longitudinal movement of the inner member relative to the outer member is controllable by rotational movement of the inner member relative to the outer member.

26. The catheter of claim 19, wherein the expandable member is configured to engage with a vessel wall of a patient when the expandable member is in the expanded configuration.

27. The catheter of claim 26, wherein when the vessel wall defines a curved shape and when the expandable member is engaged with the vessel wall, the expandable member is configured to deflect a portion of the elongated body distal to the expandable member.

* * * * *